(12) United States Patent
Kitagawa et al.

(10) Patent No.: US 7,718,623 B2
(45) Date of Patent: May 18, 2010

(54) IMMUNOSTIMULATORY OLIGONUCLEOTIDE THAT INDUCES INTERFERON ALPHA

(75) Inventors: Harukazu Kitagawa, Fukui (JP); Sumiko Iho, Fukui (JP); Takasumi Matsuki, Fukui (JP); Saburo Yamamoto, Koganei (JP)

(73) Assignees: Emori & Co., Ltd., Fukui-shi (JP); University of Fukui, Fukui-shi (JP)

( * ) Notice: Subject to any disclaimer, the term of this patent is extended or adjusted under 35 U.S.C. 154(b) by 0 days.

(21) Appl. No.: 10/590,761

(22) PCT Filed: Feb. 25, 2005

(86) PCT No.: PCT/JP2005/003693

§ 371 (c)(1),
(2), (4) Date: Aug. 24, 2006

(87) PCT Pub. No.: WO2005/083076

PCT Pub. Date: Sep. 9, 2005

(65) Prior Publication Data

US 2007/0179101 A1 Aug. 2, 2007

(30) Foreign Application Priority Data

Feb. 27, 2004 (JP) .............................. 2004-053795

(51) Int. Cl.
*A01N 43/04* (2006.01)
*A61K 31/70* (2006.01)
*C07H 21/04* (2006.01)
*A61K 39/38* (2006.01)

(52) U.S. Cl. ................. 514/44; 536/22.1; 536/23.1; 536/24.1; 424/184.1; 424/278.1

(58) Field of Classification Search ................ None
See application file for complete search history.

(56) References Cited

U.S. PATENT DOCUMENTS

| | | |
|---|---|---|
| 2003/0050268 A1 | 3/2003 | Krieg et al. |
| 2003/0087848 A1 | 5/2003 | Bratzler et al. |
| 2003/0091593 A1 * | 5/2003 | Bachmann et al. ....... 424/204.1 |
| 2003/0099668 A1 * | 5/2003 | Bachmann et al. ....... 424/204.1 |

FOREIGN PATENT DOCUMENTS

| | | | |
|---|---|---|---|
| EP | 468520 A2 * | 1/1992 | |
| JP | 2002-510644 | 4/2002 | |
| JP | 2002-517156 | 6/2002 | |
| JP | 2003-510290 | 3/2003 | |
| WO | WO 98/55495 | 12/1998 | |
| WO | WO 99/51259 | 10/1999 | |
| WO | WO0202172 A1 * | 1/2002 | |
| WO | WO 03/024480 A2 | 3/2003 | |
| WO | WO 03/024481 A3 | 3/2003 | |
| WO | WO 2004/000351 A1 | 12/2003 | |

OTHER PUBLICATIONS

Takauji et al. 2002, Journal of Leukocyte Biology, vol. 72, 1011-1019.*
International Search Report, dated Jun. 14, 2005, corresponding to PCT/JP2005/003693.
Kuramoto, et al., "Oligonucleotide Sequences Required for Natural Killer Cell Activation," Jpn. J Cancer Res., vol. 83, pp. 1128-1131, Nov. 1992.
Grug, et al., "Identification of CpG oligonucleotide sequences with high induction of IFN-alpha/bata in plasmacytoid dendritic cells," Eur. J. Immunol., vol. 31, pp. 2154-2163, 2001.
Iho, S., et al., *Oligodeoxynucleotides Containing Palindrome Sequences with Internal 5'-CpG-3' Act Directly on Human NK and Activated T Cells to Induce IFN-γ Production in Virto*, The The Journal of Immunology, (1999), pp. 3642-3652.
Tokunaga, T. et al., *Antihumor Activity of Deoxyribonucleic Acid Fraction From Mycobacterium bovis BCG. I. Isolation, Physicochemical Characterization, and Antitumor Activity*, J. Natl. Cancer Inst., vol. 72, No. 4, Apr. 1984, pp. 955-962.
Yamamoto, S. et al., *Unique Palindromic Sequences in Synthetic Oligonucleotides Are Required to Induce INF and Augment INF-Mediated Natural Killer Activity*, The Journal of Immunology, vol. 148, No. 12, Jun. 15, 1992, pp. 4072-4076.
Krieg AM. et al., *CpG motifs in bacterial DNA trigger direct B-cell activation*, Letters To Nature, vol. 374, Apr. 6, 1995, pp. 546-549.
Verthelyi, D. et al., *Differential signaling by CpG DNA in Cs and B cells: not just TLR9*, Trends in Immunology, vol. 24, No. 10, Oct. 2003, pp. 519-522.
Ballas ZK. et al., *Induction of NK Activity in Murine and Human Cells by CpG Motifs in Oligodeoxynucleotides and Bacterial DNA*, The Journal of. Immunology., vol. 157, 1996, pp. 1840-1845.
Boggs RL. et al., *Characterization and Modulation of Immune Stimulation by Modified Oligonucleotides*, Antisense & Nucleic Acid Drug Development, vol. 7, 1997, pp. 461-471.
Klinman DM. et al., *CpG motifs present in bacterial DNA rapidly induce lymphocytes to secrete , interleukin 6, interleukin 12, and interferon gamma*, Proc. Natl. Acad. Sci. U.S.A., vol. 93, Apr. 1996, pp. 2879-2883.

(Continued)

*Primary Examiner*—Janet L. Epps-Smith
(74) *Attorney, Agent, or Firm*—Christie, Parker & Hale LLP.

(57) ABSTRACT

An immunostimulatory oligonucleotide that is represented by the general formula 5'-Gm-GACGATCGTC-Gn-3' or 5'-Gm-CACGATCGTG-Gn-3' (in the formula, m and n are each independently an integer from 1 to 9 and m+n=10) and that comprises any of the following base sequences: GGAC-GATCGTCGGGGGGGG (SEQ. ID. NO.: 1), GGGAC-GATCGTCGGGGGGG (SEQ. ID. NO.: 2), GGGGAC-GATCGTCGGGGGG (SEQ. ID. NO.: 3), GGGGGGGACGATCGTCGGGG (SEQ ID NO: 4), GGGGGGGGACGATCGTCGGG (SEQ. ID. NO.: 5), GGGGGGGGGACGATCGTCGG (SEQ. ID. NO.: 6), GGGGGGGGGGACGATCGTCG (SEQ. ID. NO.: 7), and GGGGGGGGGCACGATCGTGG (SEQ. ID. NO.: 8).

4 Claims, 10 Drawing Sheets

OTHER PUBLICATIONS

Halpern, M.D., et al., *Bacterial DNA Induces Murine Interferon-γ Production by Stimulation of Interleukin-12 and Tumor Necrosis Factor-α*, Cellular Immunology, vol. 167, Article No. 0009, 1996, pp. 72-78.

Bohle, B. et al., *Oligodeoxynucleotides containing CpG motifs induce IL-12, IL-18 and IFN-γ production in cells from allergic individuals and inhibit IgE synthesis* in vitro, Eur. J. Immunol., vol. 29, 1999, pp. 2344-2353.

Iho, S. et al., *Oligodeoxynucleotides Containing Palindrome Sequences with Internal 5'-CpG-3' Act Directly on Human NK and Activated T Cells to Induce IFN-γ Production* in Vitro, The Journal of Immunology, vol. 163, 1999, pp. 3642-3652.

Hartmann, G. et al., *Delineation of a CpG Phosphorothioate Oligodeoxynucleotide for Activating Primate Immune Responses* In Vitro *and* In Vivo, The Journal of Immunology, vol. 164, 2000, pp. 1617-1624.

Hemmi, H. et al., *A Toll-like receptor recognizes bacterial DNA*, letters to nature, vol. 408, Dec. 2000, pp. 740-745.

Hornung, V. et al., *Quanttative Expression of Toll-Like Receptor 1-10 mRNA in Cellular Subsets of Human Peripheral Blood Mononuclear Cells and Sensitivity to CpG Oligodeoxynucleotides*, The Journal of Immunology, vol. 168, 2002, pp. 4531-4537.

Hartmann, G. et al., *Mechanism and Function of a Newly Identified CpG DNA Motif in Human Primary B Cells*, The Journal of Immunology, vol. 164, 2000, pp. 944-952.

Takauji, R. et al., *CpG-=DNA-induces IFN-α production involves p38 MAPK-dependent STAT1 phosphorylation in human plasmacytoid dendritic cell precursors*, Journal of Leukocyte Biology., vol. 72, Nov. 2002, pp. 1011-1019.

Halpern, M.D., et al., In vitro *inhibition of murine IFNγ production by phosphorothioate deoxyguanosine oligomers*, Immunopharmacology, vol. 29, 1995, pp. 47-52.

Chace, J., et al., *Bacterial DNA-Induced NK Cell IFN-γ Production in Dependent on Macrophage Secretion of IL-12*, Clinical Immunology and Immunopathology, vol. 84, No. 2, Aug. 1997, pp. 185-193, Article No. II974380.

\* cited by examiner

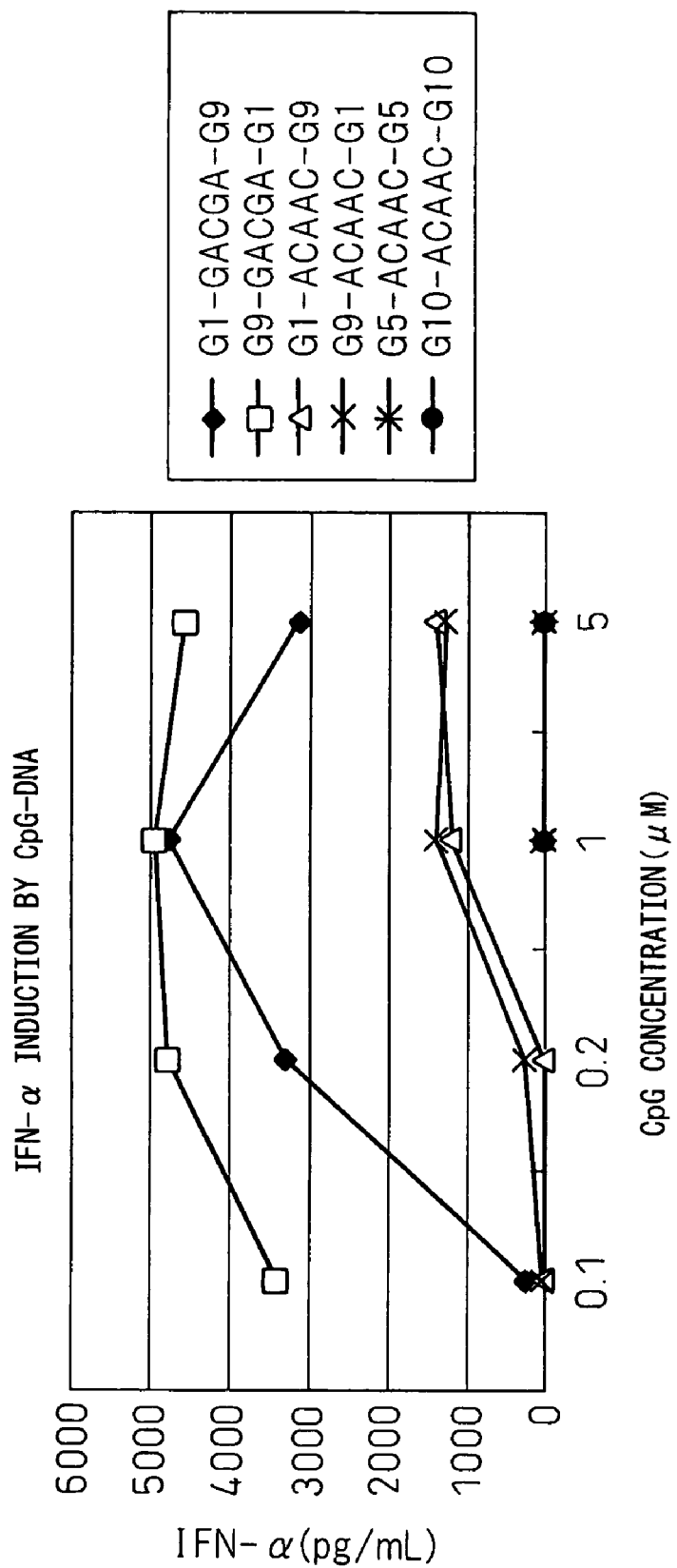

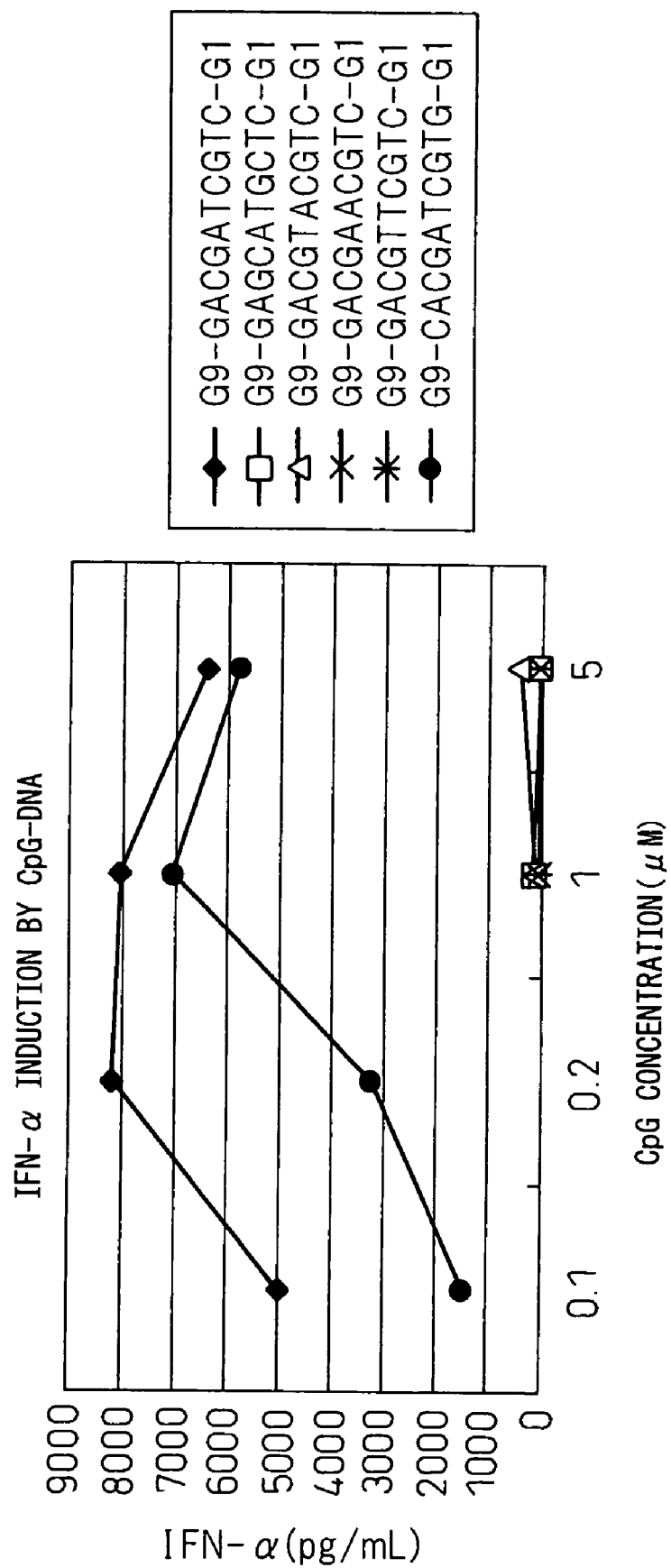

SEQUENCE LISTING

```
<160> NUMBER OF SEQ ID NOS: 62

<210> SEQ ID NO 1
<211> LENGTH: 30
<212> TYPE: DNA
<213> ORGANISM: Artificial sequence
<220> FEATURE:
<223> OTHER INFORMATION: modified Sequence encoding BCG protein
<220> FEATURE:
<221> NAME/KEY: misc_feature
<222> LOCATION: (7)..(12)
<223> OTHER INFORMATION: n is a, c, g, or t

<400> SEQUENCE: 1
accgatnnnn nngccggtga cggcaccacg                                    30

<210> SEQ ID NO 2
<211> LENGTH: 20
<212> TYPE: DNA
<213> ORGANISM: Artificial Sequence
<220> FEATURE:
```

```
<223> OTHER INFORMATION: sequence of CpG DNA that is active in mice

<400> SEQUENCE: 2
gagaacgctc gaccttcgat                                                 20

<210> SEQ ID NO 3
<211> LENGTH: 20
<212> TYPE: DNA
<213> ORGANISM: Artificial Sequence
<220> FEATURE:
<223> OTHER INFORMATION: sequence of CpG DNA that induces IFN-g
      production

<400> SEQUENCE: 3
tccatgacgt tcctgatgct                                                 20

<210> SEQ ID NO 4
<211> LENGTH: 18
<212> TYPE: DNA
<213> ORGANISM: Artificial Sequence
<220> FEATURE:
<223> OTHER INFORMATION: Antisense DNA that activates NK cells

<400> SEQUENCE: 4
tctcccagcg tgcgccat                                                   18

<210> SEQ ID NO 5
<211> LENGTH: 20
<212> TYPE: DNA
<213> ORGANISM: Artificial Sequence
<220> FEATURE:
<223> OTHER INFORMATION: CpG DNA reported to activate human B cells

<400> SEQUENCE: 5
ttgcttccat cttcctcgtc                                                 20

<210> SEQ ID NO 6
<211> LENGTH: 30
<212> TYPE: DNA
<213> ORGANISM: Artificial Sequence
<220> FEATURE:
<223> OTHER INFORMATION: cDNA encoding BCG protein
<220> FEATURE:
<221> NAME/KEY: misc_feature
<222> LOCATION: (7)..(12)
<223> OTHER INFORMATION: n is a, c, g, or t

<400> SEQUENCE: 6
accgatnnnn nngccggtga cggcaccacg                                      30

<210> SEQ ID NO 7
<211> LENGTH: 30
<212> TYPE: DNA
<213> ORGANISM: Artificial Sequence
<220> FEATURE:
<223> OTHER INFORMATION: cDNA encoding BCG protein

<400> SEQUENCE: 7
accgataacg ctgccggtga cggcaccacg                                      30

<210> SEQ ID NO 8
<211> LENGTH: 30
<212> TYPE: DNA
<213> ORGANISM: Artificial Sequence
<220> FEATURE:
<223> OTHER INFORMATION: cDNA encoding the BCG protein mod

<400> SEQUENCE: 8
accgataacg tcgccggtga cggcaccacg					30

<210> SEQ ID NO 9
<211> LENGTH: 30
<212> TYPE: DNA
<213> ORGANISM: Artificial Sequence
<220> FEATURE:
<223> OTHER INFORMATION: cDNA encoding for the BCG protein modified to
      enhance IFN-g-inducing activity

<400> SEQUENCE: 9
accgatcgat cggccggtga cggcaccacg					30

<210> SEQ ID NO 10
<211> LENGTH: 30
<212> TYPE: DNA
<213> ORGANISM: Artificial Sequence
<220> FEATURE:
<223> OTHER INFORMATION: cDNA encoding the BCG protein modified to enhance IFN-g-inducing activity

<400> SEQUENCE: 10
gggggggggg gacgatcgtc gggggggggg 30

<210> SEQ ID NO 11
<211> LENGTH: 30
<212> TYPE: DNA
<213> ORGANISM: Artificial Sequence
<220> FEATURE:
<223> OTHER INFORMATION: Unmodified CpG palindrome

<400> SEQUENCE: 11
gggggggggg ggaacgttgg gggggggggg 30

<210> SEQ ID NO 12
<211> LENGTH: 10
<212> TYPE: DNA
<213> ORGANISM: Artificial Sequence
<220> FEATURE:
<223> OTHER INFORMATION: Core sequence of CpG DNA

<400> SEQUENCE: 12
gacgatcgtc 10

<210> SEQ ID NO 13
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 13
ggacgatcgt cggggggggg 20

<210> SEQ ID NO 14
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 14
gggacgatcg tcgggggggg 20

<210> SEQ ID NO 15
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 15
ggggacgatc gtcggggggg                                              20

<210> SEQ ID NO 16
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 16
gggggggacg atcgtcgggg                                              20

<210> SEQ ID NO 17
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 17 gggggggggac gatcgtcggg                                             20

<210> SEQ ID NO 18
<211> LENGTH: 20
<212> TYPE: DNA
<213> ORGANISM: Artificial Sequence
<220> FEATURE:
<223> OTHER INFORMATION: Immunotimulatory oligonucleotide

<400> SEQUENCE: 18
ggggggggga cgatcgtcgg                                              20

<210> SEQ ID NO 19
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 19
gggggggggg acgatcgtcg                                              20

<210> SEQ ID NO 20
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 20 ggggggggc acgatcgtgg                                               20

<210> SEQ ID NO 21
<211> LENGTH: 11
<212> TYPE: DNA
<213> ORGANISM: Artificial Sequence
<220> FEATURE:
<223> OTHER INFORMATION: Core sequence of CpG DNA modified by adding -continued poly G at 3' end

<400> SEQUENCE: 21
gacgatcgtc g                                                                    11

<210> SEQ ID NO 22
<211> LENGTH: 12
<212> TYPE: DNA
<213> ORGANISM: Artificial Sequence
<220> FEATURE:
<223> OTHER INFORMATION: Core sequence of CpG DNA modified by adding
    poly G at 3' end

<400> SEQUENCE: 22
gacgatcgtc gg                                                                12

<210> SEQ ID NO 23
<211> LENGTH: 13
<212> TYPE: DNA
<213> ORGANISM: Artificial Sequence
<220> FEATURE:
<223> OTHER INFORMATION: Core sequence of CpG DNA modified by adding
    poly G at 3' end

<400> SEQUENCE: 23
gacgatcgtc ggg                                                            13

<210> SEQ ID NO 24
<211> LENGTH: 14
<212> TYPE: DNA
<213> ORGANISM: Artificial Sequence
<220> FEATURE:
<223> OTHER INFORMATION: Core sequence of CpG DNA modified by adding
    poly G at 3' end

<400> SEQUENCE: 24
gacgatcgtc gggg                                                       14

<210> SEQ ID NO 25
<211> LENGTH: 15
<212> TYPE: DNA
<213> ORGANISM: Artificial Sequence
<220> FEATURE:
<223> OTHER INFORMATION: Core sequence of CpG DNA modified by adding
    poly G at 3' end

<400> SEQUENCE: 25
gacgatcgtc ggggg                                                15

<210> SEQ ID NO 26
<211> LENGTH: 16
<212> TYPE: DNA
<213> ORGANISM: Artificial Sequence
<220> FEATURE:
<223> OTHER INFORMATION: Core sequence of CpG DNA modified by adding
    poly G at 3' end

<400> SEQUENCE: 26
gacgatcgtc gggggg                                           16

<210> SEQ ID NO 27
<211> LENGTH: 17
<212> TYPE: DNA
<213> ORGANISM: Artificial Sequence
<220> FEATURE:
<223> OTHER INFORMATION: Core sequence of CpG DNA modified by adding
    poly G at 3' end

```
<400> SEQUENCE: 27
gacgatcgtc ggggggg                                                      17

<210> SEQ ID NO 28
<211> LENGTH: 18
<212> TYPE: DNA
<213> ORGANISM: Artificial Sequence
<220> FEATURE:
<223> OTHER INFORMATION: Core sequence of CpG DNA modified by adding
      poly G at 3' end

<400> SEQUENCE: 28
gacgatcgtc gggggggg                                                     18

<210> SEQ ID NO 29
<211> LENGTH: 19
<212> TYPE: DNA
<213> ORGANISM: Artificial Sequence
<220> FEATURE:
<223> OTHER INFORMATION: Core sequence of CpG DNA modified by adding
      poly G at 3' end

<400> SEQUENCE: 29
gacgatcgtc ggggggggg                                                    19

<210> SEQ ID NO 30
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' end

<400> SEQUENCE: 30
gacgatcgtc gggggggggg                                                   20

<210> SEQ ID NO 31
<211> LENGTH: 15
<212> TYPE: DNA
<213> ORGANISM: Artificial Sequence
<220> FEATURE:
<223> OTHER INFORMATION: Core sequence of CpG DNA modified by adding
      poly G at 5' end

<400> SEQUENCE: 31 gggggggacga tcgtc                                                       15

<210> SEQ ID NO 32
<211> LENGTH: 16
<212> TYPE: DNA
<213> ORGANISM: Artificial Sequence
<220> FEATURE:
<223> OTHER INFORMATION: Core sequence of CpG DNA modified by adding
      poly G at 5' end

<400> SEQUENCE: 32 ggggggggacg atcgtc                                                      16

<210> SEQ ID NO 33
<211> LENGTH: 17
<212> TYPE: DNA
<213> ORGANISM: Artificial Sequence
<220> FEATURE:
<223> OTHER INFORMATION: Core sequence of CpG DNA modified by adding
      poly G at 5' end
```

```
<400> SEQUENCE: 33 gggggggggac gatcgtc                                              17

<210> SEQ ID NO 34
<211> LENGTH: 18
<212> TYPE: DNA
<213> ORGANISM: Artificial Sequence
<220> FEATURE:
<223> OTHER INFORMATION: Core sequence of CpG DNA modified by adding
      poly G at 5' end

<400> SEQUENCE: 34 gggggggggga cgatcgtc                                             18

<210> SEQ ID NO 35
<211> LENGTH: 19
<212> TYPE: DNA
<213> ORGANISM: Artificial Sequence
<220> FEATURE:
<223> OTHER INFORMATION: Core sequence of CpG DNA modified by adding
      poly G at 5' end

<400> SEQUENCE: 35
gggggggggg acgatcgtc                                             19

<210> SEQ ID NO 36
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 5' end

<400> SEQUENCE: 36
gggggggggg gacgatcgtc                                            20

<210> SEQ ID NO 37
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 37
gacgatcgtc gggggggggg                                            20

<210> SEQ ID NO 38
<211> LENGTH: 21
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 38
ggacgatcgt cggggggggg g                                          21

<210> SEQ ID NO 39
<211> LENGTH: 22
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 39
```

```
gggacgatcg tcgggggggg gg                                              22
```

<210> SEQ ID NO 40
<211> LENGTH: 23
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 40

```
ggggacgatc gtcgggggggg ggg                                            23
```

<210> SEQ ID NO 41
<211> LENGTH: 24
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 41

```
gggggacgat cgtcggggggg gggg                                           24
```

<210> SEQ ID NO 42
<211> LENGTH: 25
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 42

```
ggggggacga tcgtcggggg ggggg                                           25
```

<210> SEQ ID NO 43
<211> LENGTH: 30
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 43

```
gggggggggg gacgatcgtc gggggggggg                                      30
```

<210> SEQ ID NO 44
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 44

```
gacgatcgtc gggggggggg                                                 20
```

<210> SEQ ID NO 45
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 45 ggggggacgat cgtcgggggg                                      20

<210> SEQ ID NO 46
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 46 gggggggacga tcgtcggggg                                      20

<210> SEQ ID NO 47
<211> LENGTH: 20
<212> TYPE: DNA
<213> ORGANISM: Artificial Sequence
<220> FEATURE:
<223> OTHER INFORMATION: Core sequence of CpG DNA modified by adding
      poly G at 3' and 5' ends

<400> SEQUENCE: 47
gggggggggg gacgatcgtc                                       20

<210> SEQ ID NO 48
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 48
acaacgttgt                                                  10

<210> SEQ ID NO 49
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 49
gacaacgttg tggggggggg                                       20

<210> SEQ ID NO 50
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 50
gggggacaac gttgtggggg                                       20

<210> SEQ ID NO 51
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 51
ggggggggga caacgttgtg                                       20

<210> SEQ ID NO 52
<211> LENGTH: 30
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 52
gggggggggg acaacgttgt gggggggggg                                          30

<210> SEQ ID NO 53
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 53
gagcatgctc                                                                10

<210> SEQ ID NO 54
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 54
gacgaacgtc                                                                10

<210> SEQ ID NO 55
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 55
gacgttcgtc                                                                10

<210> SEQ ID NO 56
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 56
gacgtacgtc                                                                10

<210> SEQ ID NO 57
<211> LENGTH: 10
<212> TYPE: DNA
<213> ORGANISM: Artificial Sequence
<220> FEATURE:
<223> OTHER INFORMATION: Modified core sequence of CpG DNA

<400> SEQUENCE: 57
cacgatcgtg                                                                10

<210> SEQ ID NO 58
<211> LENGTH: 20
<212> TYPE: DNA
<213> ORGANISM: Artificial Sequence
<220> FEATURE:

-continued

```
<223> OTHER INFORMATION: Modified core sequence of CpG DNA with poly G
      added at 3' and 5'ends

<400> SEQUENCE: 58
gggggggggg agcatgctcg                                               20

<210> SEQ ID NO 59
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 59
gggggggggg acgtacgtcg                                               20

<210> SEQ ID NO 60
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 60
gggggggggg acgaacgtcg                                               20

<210> SEQ ID NO 61
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 61
gggggggggg acgttcgtcg                                               20

<210> SEQ ID NO 62
<211> LENGTH: 20
<212> TYPE: DNA
<213> ORGANISM: Artificial Sequence
<220> FEATURE:
<223> OTHER INFORMATION: Modified core sequence of CpG DNA with poly G
      added at 3' and 5' ends

<400> SEQUENCE: 62 ggggggggggc acgatcgtgg                                              20
```

1

IMMUNOSTIMULATORY OLIGONUCLEOTIDE THAT INDUCES INTERFERON ALPHA

CROSS-REFERENCE TO RELATED APPLICATION

This application is a National Phase Patent Application of International Application Number PCT/JP2005/003693, filed on Feb. 25, 2005, which claims priority of Japanese Patent Application Number 2004-053795, filed on Feb. 27, 2004.

TECHNICAL FIELD

The present invention relates to a sequence of an oligonucleotide having an activity, of inducing interferon alpha (IFN-α), more than ten-fold as potent as the activity retained by conventional CpG DNA.

BACKGROUND ART

The discovery of the immunostimulatory activity of bacterial DNA and the base sequence: A specific base sequence (CpG DNA) containing an unmethylated cytocine/guanine dinucleotide (5'-CpG-3') that occurs at high incidence in bacterial DNA is recognized by Toll-like receptor 9 (TLR9) and thus activates the immune system of a mammal to induce the Th1 immune reaction. It was reported by Tokunaga/Yamamoto et al. (Tokunaga T. et al., J. Natl. Cancer Inst. 72: 955-62, 1984) that the DNA fraction of BCG induces the production of type I interferon (IFN) and the subsequent activation of NK cells induced thereby and thus exhibit anti-cancer effect. In a series of studies, the investigators identified a palindrome type CpG DNA that is frequently found in bacterial DNA as the active sequence (Yamamoto S. et al., J. Immunol. 148: 4072-6, 1992). Several groups have demonstrated the immunostimulatory activity on mouse and human B cells by *Escherichia coli* DNA or non-antisense DNA, and Krieg et al. (Krieg A M. et al., Nature 374: 546-9, 1995) reported 5'-PuPuCpGPyPy-3' that has unmethylated CpG and that is flanked by specific bases as a mouse B cell-activating motif. Other unique sequences of CpG DNA that exhibit an immunostimulatory activity have been presented and, at present, they are roughly grouped into the IFN induction type, the B cell activation type, and the mixed type (Verthelyi D. et al., Trends Immunol. 24: 519-22, 2003).

On the base sequence that activates mouse NK cells: In order to identify active base sequences, the Tokunaga/Yamamoto group selected at random and synthesized base sequences of a certain length from cDNAs that encode the BCG protein. After investigating 30-chain length bases 5'-ACCGATNNNNNNGCCGGTGACGGCACCACG-3' (SEQ. ID. No. 1) (N is a complementary base pair), they thought it important that the N portions include CpG and that three consecutive bases on one side are followed by the complementary bases forming a palindrome structure (Yamamoto S. et al., J. Immunol. 148: 4072-6, 1992).

Krieg et al. discussed whether, as the mouse B cell activating motif PuPuCpGPyPy (specifically, GACGTT is potent) also has an activity of enhancing the NK activity, the important sequence for the activation of NK cells is the unmethylated CpG which is followed by a specific base, but that the motif does not have to take a palindrome sequence (Krieg A M. et al., Nature 374: 546-9, 1995; Ballas Z K. et al., J. Immunol. 157: 1840-5, 1996). Boggs et al. reported that the CpG dinucleotide alone, though required, cannot activate NK cells, and specific bases and background sequences surrounding CpG and their modifications such as thiolation or methylation define the NK cell activation by CpG DNA (Boggs R L. et al., Antisense & Nucleic Acid Drug Development 7: 461-71, 1997). For example, the thiolation of CpG DNA leads to an attenuated activity of activating NK cells.

The methylation of the active motif of CpG leads to decreased NK activity. However, depending on the base sequence of the motif, activity may be retained even after methylation of CpG. In this case, the methylation of all cytosines in CpG DNA leads to total annihilation of the activity. As the motifs of CpG DNAs so far reported to have an activity of enhancing the NK activity are not limited to palindrome or PuPuCpGPyPy and are composed of 6-chain length centering on the unmethylated CpG surrounded by specific base sequences, it is believed, the enhancement of the NK activity by CpG DNA is induced by a higher structure constructed by the entire base sequence comprising the active motif, the background sequence and modifications.

Reaction of mouse NK cells to CpG DNA requires activation: Yamamoto et al. have demonstrated that the enhancement of the NK activity by CpG DNA is mediated by type I IFN that was produced by cells other than the NK cells (Yamamoto S. et al., J. Immunol. 148: 4072-6, 1992). Klinman et al. report that the IFN-γ-producing cells in mouse spleen cells induced by CpG DNA are NK cells and the IFN-γ production is inhibited by IL-12 antibody (Klinman D M. et al., Proc. Natl. Acad. Sci. U.S.A. 93: 2879-83, 1996). Halpern et al. demonstrated that bacterial DNA or CpG DNA stimulate monocytes/macrophages to induce the production of IL-12 or TNF-α, with a result that IFN-γ is produced by non-adhering cells (Halpern M D. et al., Cellular Immunol. 167: 72-8, 1996).

Ballas et al. have demonstrated that NK cells respond to CpG DNA in the presence of IL-12, IFN-α/β and TNF-α, and thus the NK activity becomes enhanced. Chace et al. also report that the activation of NK cells is macrophage-dependent and that NK cells, when activated by IL-12, acquire reactivity to bacterial DNA and IFN-γ production is amplified (Balla Z K. et al., J. Immunol. 157: 1840-5, 1996). These results suggest that inactivated mouse NK cells cannot react to CpG DNA but are activated by stimulation with cytokines derived from CpG DNA-stimulated monocytes/macrophages, and thus acquires CpG DNA reactivity.

Activation of human NK cells by CpG DNA: The effect of CpG DNA is conspicuous in the mouse immune system but the reactivity is generally low in the human immune system. However, the anti-cancer activity of BCG DNA mediated by host immunity had been reported in the 1980s, and the NK activity is enhanced both in vivo and in vitro. On the other hand, human peripheral blood mononuclear cells (PBMC) produce IFN-α, IL-12 and IL-18 by stimulation with CpG DNA, and the production of IFN-γ is induced by IL-12 stimulation (Bohle B. et al., Eur. J. Immunol. 29: 2344-53, 1999). These results suggest that, in humans as well as in mice, dendritic cells and monocytes/macrophages are involved in the activation of NK cells by CpG DNA.

Iho et al. speculated that the action mechanism and the activity sequence of CpG DNA in humans are different from those in mice because stimulation of human mononuclear cells by BCG DNA does not significantly induce the production of IL-12. In fact, among the PuPuCpGPyPy type CpG DNAs that are reported to be active in mice, #1643 (gagaacgctcgaccttcgat) (SEQ. ID. No. 2) that activates B cells, #1618 (tccatgacgttcctgatgct) (SEQ. ID. No. 3) that induces IFN-γ, an antisense DNA #1758 (tctcccagcgtgcgc-cat) (SEQ. ID. No. 4) that activates NK cells, and #2105

(ttgcttccatcttcctcgtc) (SEQ. ID. No. 5) that activates human B cells were investigated for activation of NK cells with IFN-γ production as an index, but none of the sequences activated the purified human NK (CD56⁺) cells.

Thus, among cDNAs that encodes the BCG protein, ten 30-chain length DNAs (Iho S. et al., J. Immunol. 163: 3642-52, 1999), accgatNNNNNNgccggtgacggcaccacg (SEQ. ID. No. 6), that contain specific six-chain length CpG palindrome (NNNNNN) were investigated, and seven of them were found to have the IFN-γ-inducing activity. Then, mouse B cell-activating motifs aacgct and aacgtc that are not effective for the activation of human NK cells were inserted into the background sequence of CpG DNA that was activated with human NK cells to synthesize accgat*aacgct*gccggtgacggcaccacg (SEQ. ID. No. 7) and accgat*aacgtc*gccggtgacggcaccacg (SEQ. ID. No. 8) (underlined sequences were inserted), and they were investigated for activity, but no activity was recognized. This indicated that for CpG DNA to be recognized by NK cells the activity motif of CpG DNA must assume a palindrome structure.

However, as even for the same sequence there was variation in the amount of IFN-γ produced between donors, and there were individual differences for the optimum sequence, 12-chain G was added (g12CGA) on both sides of the underlined palindrome portion CGATCG for the weaker accgat*c-gatcg*gccggtgacggcaccacg (SEQ. ID. No. 9) and they were investigated. The reason for adding G is that poly G has a high affinity for cells and stabilizes the higher structure of DNA. As expected, G addition enhanced the IFN-γ-inducing activity of CGATCG. When sequences having further higher activity were investigated, higher activity was noted in a full-length 30-chain g10GACGA (GGGGGGGGGGGGACGATCGTCGGGGGGGGGG (SEQ. ID. No. 10)) in which the palindrome portion of g12CGA was repeat-extended to 10 bases and 10-chain G was added to each side chain.

G10GACGA is a sequence that has the most potent activity among the human NK cell-activating sequences reported in 1999. As described below, though NK cells when activated exhibit a high reactivity to CpG DNA, the induction of IFN-γ by G10GACGA does not disappear after neutralization of non-NK cell-derived cytokines with anti-IFN-α antibody etc. and, therefore, it is thought that human NK cells are equipped with an ability to react to CpG DNA. IFN-γ produced by G10GACGA enhances the NK activity through an autocrine reaction and induces the expression of CD69 and HLA-ABC.

CpG DNA reactivity of activated human NK cells: Activated human NK cells have a higher reactivity to CpG DNA as compared to unactivated NK cells (Iho S. et al., J. Immunol. 163: 3642-52, 1999). This is in agreement with the fact that the expression of TLR9, a CpG DNA receptor, is weak in non-stimulated NK cells (Krug A. et al., J. Immunol. 31: 2154-63, 2001). However, there are no reports that TLR9 is induced by the activation of NK cells, and the mechanism in which CpG DNA reactivity is enhanced by activation is unknown. Furthermore, as NK cells activated by IL-2 also react to the non-palindrome type CpG DNA (Iho S. et al., J. Immunol. 163: 3642-52, 1999), the sequence selectivity of CpG DNA must be investigated.

The difference in CpG DNA reactivity between human NK cells and mouse NK cells: Human NK cells, even if unactivated, react to CpG DNA, but mouse NK cells do not react to CpG DNA unless activated. The reason for this difference in reactivity is not known. Ballas et al. (Ballas Z K. et al., J. Immunol. 157: 1840-5, 1996) investigated a CpG palindrome having a G-repeated sequence on both of 5'-end and 3'-end, but it could not activate mouse NK cells nor human NK cells.

2216 of Krug et al. (Krug A. et al., J. Immunol. 31: 2154-63, 2001) has GACGATCGTC but does not activate human NK cells. The difference between the present g10GACGA and the CpG DNA of Ballas/Krug et al. is the number of poly G added and modification thereof. The former is an unmodified type, while part of the latter has been thiolated.

The thiolation of DNA enhances resistance to DNase, but lowers the immunostimulatory activity because interaction with DNA-binding protein is weakened. Thus, it is likely that thiol modification may cause low CpG reactivity of NK cells. On the other hand, some unmodified CpG palindrome having poly G in the background sequence like ggggggggggggaacgt-tggggggggggg (SEQ. ID. No. 11) have no activity (Iho S. et al., J. Immunol. 163: 3642-52, 1999). The sequence and length of the palindrome bases are considered important elements. It was later reported that the reactivity of human cells to the mouse activation motif is low, and reactivity to CpG DNA in primates was found to be different between humans, chimpanzees and monkeys, and therefore it is generally accepted that there is a species difference in CpG DNA reactivity (Hartmann G. et al., J. Immunol. 164: 1617-24, 2000). It is also becoming clearer that the CpG DNA sequence has cell selectivity (Verthelyi D. et al., Trends Immunol. 24: 519-22, 2003).

Intracellular incorporation of CpG DNA and recognition by TLR9: A recent study has revealed that CpG DNA is a ligand for TLR9 (Hemmi H. et al., Nature 408: 740-5, 2000). In an examination with a confocal microscope, it was shown that the binding of CpG DNA to the cell membrane and its incorporation into the cell are not sequence-specific and CpG DNA is localized together with TLR9 in the endosome. Thus, it is believed that CpG DNA is incorporated into the cell by endocytosis and it is recognized by TLR9 in the endosome. In order for CpG DNA to exhibit its biological activity, it must be modified in some way in the endosome. In the process of CpG DNAs being incorporated into the cell and recognized by TLR9 and of TLR9 signal transduction, a plurality of molecules need to work in concerted actions and research is on going.

Signal transduction of CpG DNA: While the incorporation of CpG DNA into the cell is effected in a CpG-nonspecific manner, the process from recognition by TLR9 to the expression of biological activity is CpG-specific. Cells that strongly express TLR9 in human peripheral blood are mainly B cells and plasmacytoid dendritic cells (PDC) (Hornung V. et al., J. Immunol. 168: 4531-7, 2002). In CpG DNA-stimulated B cells, the activation of p38 and JNK occurs very early and the ability of a transcription factor AP-1 to bind to DNA increases and the transcription of related genes are enhanced Hartmann G. et al., J. Immunol. 164: 944-52, 2000).

In PDC, CpG DNA is incorporated by endocytosis and then is recognized by TLR9 thereby to activate p38 MAPK. Subsequently, STAT1 is phosphorylated to form ISGF3 together with STAT2 and IRF-9. This leads to the enhanced transcription of the IRF-7 gene, and the IRF-7 thus produced induces the transcription of the IFN-α gene to produce IFN-α. Furthermore, extracellularly secreted IFN-α is fed back to stimulate the JAK-STAT pathway and thus a large quantity of IFN-α is produced (Takauji R. et al., J. Leukoc. Biol. 72: 1011-1019, 2002).

Significance of the poly G-added palindrome CpG DNA: CpG DNA is recognized by target cells centering on at least six-chain bases containing the CpG dinucleotide, and the activity greatly varies with slight differences in not only the core sequence but the surrounding bases (background bases). In order to directly induce PDC to produce IFN-α and to produce a large quantity of IFN-α by an autocrine reaction, it is important that the core sequence of CpG DNA takes a palindrome structure. Then, the length and the position and the types of bases on both sides are mentioned as factors that affect activity. In fact, the consecutive addition of G having a high affinity for the cell membrane to the core sequence "GACGATCGTC" (SEQ. ID. No. 12) induces a high activity.

On the other hand, poly G per se inhibits the IFN-γ production in mouse spleen cells (Halpern M D. et al., Immunopharmacology 29: 47-52, 1995), the addition of G has a risk of affecting the loss or inhibition of activity. This, in a different perspective, means a possibility that by changing the palindrome sequence and the mode of adding G, the CpG DNA activity may be regulated and CpG DNA that selectively induce specific cytokines may be developed. In fact, the poly G-added palindrome CpG DNA strongly induces the production of IFN-α or IFN-γ in PBMC but does not induce that of IL-12 or IL-6. In a later study this sequence was termed the D or A type oligo, and G10GACGA reported by Kuramoto/Iho et al. in 1992 (Kuramoto E. et al., Jpn. J. Cancer Res. 83: 1128-31, 1992) and 1999 is included in this type.

A DNA sequence composed of consecutive guanines is called a poly G sequence or a G-quartet, and enhances the incorporation of CpG DNA into the cell. Thus, it is believed that in the poly G-added palindrome CpG DNA a double stranded overlapping region is formed by the palindrome base sequences, and the poly G added to the end thereof enhances resistance to nuclease digestion and stabilize the higher structure of DNA so that activity may be efficiently developed. In fact, the CpG palindrome DNA in which poly G was introduced has a high activity of inducing IFN-α or CXCL10. Thus, it is thought that a Th1 immune reaction is efficiently induced and thus usefulness for application to the treatment of cancer, allergies and infections may be expected. In animal experiments, a thiol-modified CpG DNA is usually used, which is reported to bring about fatal side effects. From these facts, it is important to develop an unmodified poly G-added palindrome CpG DNA that is safe and has a highly effective Th1 immunostimulatory activity.

Patent document 1: Kohyo (National Publication of Translated Version) No. (A) 2002-510644

Patent document 2: Kohyo (National Publication of Translated Version) No. (A) 2002-517156

Non-patent document 1: Tokunaga T. et al., J. Natl. Cancer Inst. 72: 955-62, 1984

Non-patent document 2: Yamamoto S. et al., J. Immunol. 148: 4072-6, 1992

Non-patent document 3: Krieg A M. et al., Nature 374: 546-9, 1995

Non-patent document 4: Verthelyi D. et al., Trends Immunol. 24: 519-22, 2003

Non-patent document 5: Ballas Z K. et al., J. Immunol. 157: 1840-5, 1996

Non-patent document 6: Boggs R L. et al., Antisense & Nucleic Acid Drug Development 7: 461-71, 1997

Non-patent document-7: Klinmann D M. et al., Proc. Natl. Acad. Sci. U.S.A. 93: 2879-83, 1996

Non-patent document 8: Halpern M D. et al., Cellular Immunol. 167: 72-8, 1996

Non-patent document 9: Bohle B. et al., Eur. J. Immunol. 29: 2344-53, 1999

Non-patent document 10: Iho S. et al., J. Immunol. 163: 3642-52, 1999

Non-patent document 11: Krug A. et al., J. Immunol. 31: 2154-63, 2001

Non-patent document 12: Hornung V. et al., J. Immunol. 168: 4531-7, 2002

Non-patent document 13: Hartmann G. et al., J. Immunol. 164: 1617-24, 2000

Non-patent document 14: Hemmi H. et al., Nature 408: 740-5, 2000

Non-patent document 15: Hartmann G. et al., J. Immunol. 164: 944-52, 2000

Non-patent document 16: Takauji R. et al., J. Leukoc. Biol. 72: 1011-1019, 2002

Non-patent document 17: Halpern M D. et al., Immunopharmacology 29: 47-52, 1995

Non-patent document 18: Kuramoto E. et al., Jpn. J. Cancer Res. 83: 1128-31, 1992

DISCLOSURE OF THE INVENTION

Unmodified oligonucleotides are not very resistant to nuclease digestion. However, the administration to mice of thiol-modified CpG DNA having an enhanced DNase resistance causes fatal side effects. The present invention provides an unmodified CpG DNA that has few side effects, and thus a potential for clinical applications, and a potent Th1 immunostimulatory activity.

In the investigation on the above problems, the present inventors have found that an immunostimulatory oligonucleotide composition having an unmodified base sequence represented by the general formula 5'-Gm-GACGATCGTC-Gn-3' (m=1 to 3, n=9 to 7 and m=7 to 9, n=3 to 1, m+n=10) has a potent IFN-α-inducing activity. Specifically, among them, G9-GACGATCGTC-G1 and G1-GACGATCGTC-G9 and G9-CACGATCGTG-G1 were found to have a potent IFN-α-inducing activity.

The present inventors have found an unmodified CpG DNA having a Th1 immunity-enhancing activity more potent than the conventional CpG DNA by introducing poly G of an optimum length up to 10 residues to the 5'-end and the 3'-end of CpG DNA having as the basic backbone a self-complementary palindrome sequence (5'-GACGATCGTC-3') of a decamer.

It has been suggested that, in humans, the production of IFN-α and IP-10 by PDC is integral to the Th1 immune reaction. The present inventors have found that CpG DNA causes the p38 MAPK activation by PDC with a result that IFN-α and IP-10 are induced. The extracellularly secreted IFN-α is feedbacked to PDC and thus further large quantities of IFN-α and IP10 are produced. Thus, though the subject is preferably purified PDC in the screening of CpG DNA activity, PDC is a minor group in the immunocompetent cells and therefore it is not suitable as a subject cell as a means of solving the problem. TLR9 which is a CpG DNA receptor is mainly expressed in PDC and B cells in human peripheral blood, but the CpG DNA sequence has a cell selectivity and poly G-added palindrome CpG DNA acts on PDC but not on B cells. By utilizing these characteristics and investigating the CpG DNA activity using PBMC containing PDC, the activity of the poly G-added palindrome CpG DNA can be evaluated. By using PBMC as a subject, there is also an advantage that activity can be evaluated in an environment close to in vivo. Also, as the production of IFN-α by CpG DNA is accompanied by the production of IP-10, the measurement of the ability of PBMC of inducing IFN-α enables the identification of the Th1 immunity-induced CpG DNA sequence. Thus, in this invention, CpG DNA that strongly induces PBMC to produce IFN-α was used as a means for solving the problem.

Thus, the present invention provides an immunostimulatory oligonucleotide that is represented by the general formula 5'-Gm-GACGATCGTC-Gn-3' or 5'-Gm-CACGATCGTG-Gn-3' (in the formula, m and n are each independently an integer from 1 to 9 and m+n=10) and that comprises any of the following base sequences:

```
GGACGATCGTCGGGGGGGGG,     (SEQ ID NO: 13)
GGGACGATCGTCGGGGGGGG,     (SEQ ID NO: 14)
GGGGACGATCGTCGGGGGGG,     (SEQ ID NO: 15)
GGGGGGGACGATCGTCGGGG,     (SEQ ID NO: 16)
GGGGGGGGACGATCGTCGGG,     (SEQ ID NO: 17)
GGGGGGGGGACGATCGTCGG,     (SEQ ID NO: 18)
GGGGGGGGGGACGATCGTCG,     (SEQ ID NO: 19)
and
GGGGGGGGGGCACGATCGTGG     (SEQ ID NO: 20)
```

An oligonucleotide comprising GGGGGGGGGGACGATCGTCG (SEQ. ID. NO.: 19) is specifically preferred.

The present invention also provides a pharmaceutical formulation comprising as an active ingredient an immunostimulatory oligonucleotide comprising a base sequence according to any of SEQ. ID. NO.: 13 to 20. The present invention specifically provides a pharmaceutical formulation comprising as an active ingredient an immunostimulatory oligonucleotide comprising a base sequence according to SEQ. ID. NO.: 19.

The present invention also provides a pharmaceutical formulation comprising as an active ingredient an immunostimulatory oligonucleotide comprising a base sequence according to any of SEQ. ID. NO.: 13 to 20 and further comprising an immunomodulating factor. The present invention specifically provides a pharmaceutical formulation comprising, as an active ingredient, an immunostimulatory oligonucleotide comprising a base sequence according to SEQ ID NO: 19 and further comprising an immunomodulating factor. The above immunomodulating factor is for example an antigen or an adjuvant.

BRIEF EXPLANATION OF THE DRAWINGS

FIG. 13 is a graph showing the result of investigation (2) of the significance of the palindrome sequence of G9-GACGA-G1 in Example 11.

FIG. 14 is a graph showing the result of investigation of mutants of GACGATCGTC in Example 12.

BEST MODE FOR CARRYING OUT THE INVENTION

Figure 1:
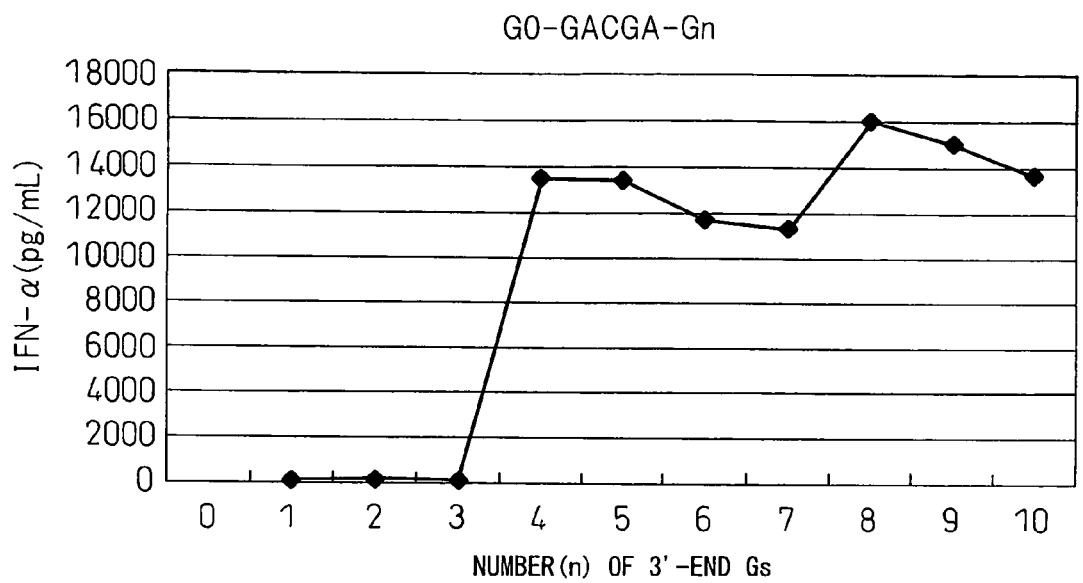
FIG. 1 is a graph showing the result of investigation of the number of Gs added (GO-GACGA-Gn) to the 3'-end in Example 1.

The core sequence of the present invention, a decanucleotide GACGATCGTC, assumes a palindrome sequence. By this core sequence being recognized by TLR9 expressed by PDC, a signal is induced and transduced with a result that IFN-α is induced. At this time, it is believed, a higher structure composed by the poly G portions at the 5'-end and the 3'-end and the core sequence define the CpG DNA activity as a TLR9 ligand. Thus, the entire base sequence in which the optimum length of poly G has been introduced into the core bases (GACGATCGTC) and the both ends thereof is the most important part of the present invention.

As the Th1 immune response is induced by the administration of CpG DNA to a living body, the present invention can be used as an anti-tumor immunopotentiating agent, a vaccine adjuvant for infections and cancers, and anti-allergy agents.

When CpG DNA is administered to a subject, natural immunity nonspecific for antigen is activated. Then, when antigen is administered after a certain period, antigen-specific Th1 immunity is strongly induced. These antigens are known substances, i.e. cells, cell extracts, proteins, peptides, polysaccharides, polysaccharide conjugates, lipids, glycolipids, carbohydrates, deoxyribonucleic acids, ribonucleic acids, virus extracts, viruses, bacteria, fungi, parasites, and allergens, or nucleic acids encoding antigen, and may be selected as appropriate depending on specific embodiments.

In the prevention and treatment of infectious diseases, the antigen is derived from pathogenic microorganisms such as infectious microorganisms, infectious viruses and infectious fungi, and is an allergen in the prevention and treatment of allergy diseases. The subject is actively exposed to these antigens. The antigen can be delivered through the colloid dispersion system. This colloid dispersion system is selected from the group consisting of a polymer complex, a nanocapsule, a microsphere, beads and a lipid-based system. The lipid-based system is preferably selected from the group consisting of an oil-in-water emulsion, a micelle, a mixed micelle and a liposome.

In another method, CpG DNA may be administered in combination with an antigen and an immunomodulating factor (including, but not limited to, a cytokine and a kemokine), or another adjuvant.

The subject is a vertebrate. Preferably the subject is human. However, in several embodiments, the subject is a non-human vertebrate. The non-human vertebrate may be selected from dogs, cats, horses, cattle, pigs, sheep, goats, chickens, primates, fish, rats, guinea pigs and mice.

CpG DNA having the peculiar sequence of the present invention is based on a discovery that it induces the production of IFN-α ten time more strongly than the unmodified CpG-containing nucleotides reported so far. This potent induction of IFN-α brings about the activation of the subsequent immunological circuit resulting in the advantageous induction and activation of the Th1 type immune response.

The induction of Th1 type cytokines resulting from CpG DNA administration causes the augmentation of cell-mediated immune response (such as are effected by NK cells, cytotoxic killer cells, Th1 helpers and memory cells). These responses are specifically useful for preventive or therapeutic vaccination against infection by viruses, fungi, protozoa, parasites and bacteria, allergic diseases, tuberculosis and tumors. CpG DNA may be utilized by mucosal administration as well. The term "cytokine" refers to an interleukin (such as IL-1, IL-2 and IL-3), an interferon (IFN-α, IFN-β, IFN-γ etc.), erythropoietin, a colony stimulating factor (such as G-CSF, M-CSF and GM-CSF), and TNF-α. The term "adjuvant" refers to a substance that, when added to an immunogenic substance, nonspecifically promotes or enhances the host immune response of the recipient exposed to this mixture.

It is known in the art that CpG DNA enhances an antigen-specific immune response by inducing the activation of the immune system, and it can be utilized in prevention and treatment of a number of diseases.

As used herein "antigen" refers to a molecule that can cause an immune response. The antigen includes, but not limited to, the following: cells, cell extracts, polysaccharides, polysaccharide conjugates, lipids, glycolipids, carbohydrates, peptides, proteins, viruses and virus extracts. The term "antigen" is any type of molecule that is recognized as foreign by a host's immune system. As the antigen, there can be mentioned, but not limited by, a cancer antigen, a microbial antigen and an allergen.

The CpG DNA of the present invention is useful for the treatment of cancer by stimulating a specific immune response against a cancer antigen. "Cancer antigen" as used herein is a compound (for example a peptide) that is associated with the surface of tumor or cancer cells, and when this compound is expressed on the antigen presenting cell, an immune response is elicited. As the cancer antigen, there can be mentioned the immunogenic portions of a tumor or a cancer, the entire tumor or the entire cancer. Such an antigen may be isolated, or prepared recombinantly or by a means known in the art. Cancers or tumors may include, but are not limited to, the following: hepatic cancer, bile duct carcinoma, brain cancer, breast cancer, cervical cancer, choriocarcinoma, colon cancer, endometrial carcinoma, esophageal carcinoma, gastric cancer, intraepidermal neoplasma, lymphoma, lung cancer, melanoma, neuroblastoma, oral cancer, ovarian cancer, pancreatic cancer, prostate cancer, rectal cancer, sarcoma, skin cancer, testicular carcinoma, thyroid cancer and renal cancer, as well as other cancers and sarcomas.

The CpG DNA of the present invention is also useful for treating infectious diseases. As used herein infectious diseases are diseases caused by the invasion of pathogenic microorganisms into the living body or the abnormal growth of the normal bacteria flora. Using CpG DNA, an antigen-specific immune response can be stimulated that can activate T cell response or B cell response to microbial antigens. The present method may be carried out similarly to those against the above tumors except the antigen is specific for the microorganism. "Microbial antigen" as used herein refers to an antigen of a microorganism, and includes, but is not limited to, infectious viruses, infections bacteria and infectious fungi.

The CpG DNA of the present invention is also useful for the prevention and treatment of allergic diseases. In this case, except that the antigen is specific for allergen, the tumor immunity treatment and the treatment of infectious diseases may be attained by the above method. At present, allergic diseases are generally treated by injection of a low dose antigen followed by increasing the dosage, i.e. injection of a high dose antigen. This procedure is thought to induce a memory immune response and to prevent a further allergic response. "Allergen" refers to a substance (antigen) that can elicit an allergic response in a susceptible subject.

"Allergy" refers to acquired hypersensitivity against a substance (allergen). Allergic diseases include, but not limited to, eczema, allergic rhinitis or allergic coryza, hay fever, bronchial asthma, urticaria and food allergy, as well as other atopic conditions. Since allergic diseases are mediated by the Th2 type immune response, CpG DNA can treat or prevent allergy by shifting the immune response of the subject from the Th2-dominant state to the Th1-dominant state.

"Subjects" include, but are not limited to, humans or dogs, cats, horses, cattle, pigs, sheep, goats, chickens, primates, fish, rats, and mice. Avians other than chickens specifically include hens, turkeys, ducks, geese, quails and pheasants. Vaccination of cultured fish is the only preventive method that can provide protection against infection by immunization for a long time. The immune system of a fish has lymphocyte subclasses having a role similar to those of lymphocyte subclasses of B cells and T cells of mammals.

The subject is exposed to antigen. As used herein the term "exposed" refers to a process in which the subject is actively exposed to the antigen in a living body or a process in which the subject is passively exposed to the antigen. The method of actively exposing the subject to the antigen is known in the art. Generally, the antigen is directly administered to the subject either systemically or locally by any means (for example, intravenous, intramuscular, oral, transdermal, mucosa, nasal, intratracheal, intradermal or subcutaneous administration). CpG DNA may be administered alone or in combination with an antigen on a regular basis. The antigen may be delivered alone or together with a carrier to the immune system of the subject. For example, as the "colloid dispersion system", there can be mentioned a polymer complex, a nanocapsule, a microsphere, beads and a lipid-based system (including an oil-in-water emulsion, a micelle, a mixed micelle and a liposome). The preferred colloid system of the present invention is liposome.

It is thought that the antigen is delivered to the subject in terms of the nucleic acid molecule encoding this antigen with a result that this antigen must be expressed in vivo. The nucleic acid encoding the antigen is operably linked to the gene expression sequence that directs the expression in eukaryotic cells. "Gene expression sequence" is any regulatory nucleotide sequence (for example, a promoter sequence or a combination of promoter-enhancer) that promotes the efficient transcription and translation of the nucleic acid encoding the antigen. Generally the gene expression sequence includes, as needed, a non-transcription sequence and a non-translation sequence (for example, TATA box, cap sequence and CAAT sequence) involved in the initiation of transcription and translation, respectively.

The nucleic acid encoding the antigen may be delivered to the immune system alone or in combination with a vector. In the broadest sense, "vector" refers to any vehicle that promotes the transfer of an antigen-encoding nucleic acid to the cells of the immune system, preferably antigen presenting cells (APC), with a result that the antigen is expressed on the surface of the APC and presented to other immunocompetent cells. The vector may contain, as needed, a gene expression sequence and the CpG DNA sequence.

CpG DNA may be directly administered to the subject or may be administered together with a nucleic acid-delivering complex. The "nucleic acid-delivering complex" means a nucleic acid molecule bound (for example, via an ionic binding or a covalent binding thereof, or encapsulated therein) to a molecule that forms a higher affinity binding to the target cell (for example, the surface of dendritic cells). As the example of the nucleic acid-delivering complex, there can be mentioned nucleic acid molecules bound to a sterol (for example, cholesterol), a lipid (for example, a cationic lipid or liposome), or a target cell-specific binding factor (for example, a ligand recognized by a target cell specific receptor).

"Palindrome sequence" means a reversed repeat sequence (i.e., a sequence like ABCDEE'D'C'B'A', in which A and A' are bases that can form a complementary base pair). Generally nucleic acid molecules are susceptible to digestion in vivo, but the CpG DNA base sequence of the present invention is considered very stable because of the palindrome sequence contained. Thus, just as double stranded DNA is very stable in a living body, part of the CpG DNA of the present invention assumes a palindrome sequence and thereby complementary base pairs can form double strands in the same molecule or between molecules. By so doing, resistance against digestion via exonuclease or endonuclease in the living body can be acquired, and the structure of CpG DNA can be stabilized.

APC includes dendritic cells (immature dendritic cells and dendritic cell precursors as well as mature dendritic cells) that can incorporate and express the antigen.

In order to be used in treatment, an appropriate useful amount of CpG DNA may be administered in a suitable dosage form (CpG DNA alone or a nucleic acid complex) to the subject by any means to be incorporated into the target cells (for example PDC). Preferred pathways for administration are, but are not limited to, oral, transdermal (subcutaneous, intradermal, intravenous, intraperitoneal, intramuscular etc.), nasal, intratracheal and mucous.

"A useful amount" of CpG DNA refers to an amount that is required and sufficient to recognize the biological effect (the production of cytokine comprising mainly IFN-α). The effective amount of CpG DNA to be administered may vary depending on the disease to be applied and its condition, the size of the subject and the like.

As a useful CpG DNA of the present invention, there can be mentioned an immunostimulatory oligonucleotide comprising any of

```
GGACGATCGTCGGGGGGGG,        (SEQ ID NO: 13)

GGGACGATCGTCGGGGGGG,        (SEQ ID NO: 14)

GGGGACGATCGTCGGGGGG,        (SEQ ID NO: 15)

GGGGGGGACGATCGTCGGG,        (SEQ ID NO: 16)

GGGGGGGGACGATCGTCGG,        (SEQ ID NO: 17)

GGGGGGGGGACGATCGTCGG,       (SEQ ID NO: 18)

GGGGGGGGGGACGATCGTCG,       (SEQ ID NO: 19)

and

GGGGGGGGGCACGATCGTGG,       (SEQ ID NO: 20)

and
``` specifically mentioned an oligonucleotide comprising GGGGGGGGGGACGATCGTCG (SEQ. ID. NO.: 19). The effective amount of CpG DNA of the present invention is determined by measuring the amount of IFN-α and various cytokines in the blood. Dosages in the range of 1 ng/kg to 100 mg/kg are considered useful (depends on the method of administration).

The formulation of the present invention is administered in a pharmaceutically acceptable solution. The solution may include usually pharmaceutically acceptable concentrations of salts, buffers, preservatives, carriers, adjuvants, and as needed other therapeutic ingredients.

This CpG DNA and the antigen may be administered per se (native) or in the form of pharmaceutically acceptable salts. When used in pharmaceutical formulations, salts must be pharmaceutically acceptable and can include, but are not limited to, salts prepared from the following acids: hydrochloric acid, hydrobromic acid, sulfuric acid, nitric acid, phosphoric acid, maleic acid, acetic acid, salicylic acid, p-toluenesulfonic acid, tartaric acid, citric acid, methansulphonic acid, formic acid, malonic acid, succinic acid, naphthalene-2-sulphonic acid, and benzene sulphonic acid. Also, these salts may be prepared as alkali metal salts or alkaline earth metals (for example sodium salts, potassium salts, or calcium salts).

Suitable buffers include the following: acetic acid and its salts, citric acid and its salts, boric acid and its salts, and phosphoric acid and its salts. Suitable preservatives include, for example, benzalkonium chloride, chlorobutanol, parabene and thimerosal.

The pharmaceutical composition of the present invention contains a useful amount of CpG DNA and an antigen (contained in a pharmaceutically acceptable carrier as needed). The term "pharmaceutically acceptable carrier" means a solid or liquid filler, a diluent or a capsule suitable for administration to humans or other vertebrates. The term "carrier" refers to a natural or synthetic organic or inorganic component that is combined with the active ingredient in order to facilitate application. The components of the pharmaceutical composition may also be mixed with the CpG DNA of the present invention in such a mode that no interactions occur that substantially reduce pharmaceutical efficiency. According to the present invention, a useful CpG DNA may be delivered in more than one CpG DNA or an antigen mixture. The mixture may comprise several CpG DNAs or antigens.

Various administration pathways may be used. The mode of administration depends on CpG DNA or the antigen selected, the condition to be treated, and the dosage to be needed for therapeutic efficacy. The best method of working the present invention clinically and experimentally is to use any pharmaceutically acceptable mode of administration.

The present invention will now be explained with reference to Examples, but it should be noted that the present invention is not limited to these examples in any way.

EXAMPLES

PBMC used in the experiment was obtained as follows: The buffy coat of peripheral blood of healthy adult humans who gave informed consented was layered on the Percoll (Pharmacia) density solution (specific gravity 1.077) and centrifuged (1,800 rpm, 20 min) to isolate peripheral blood mononuclear cells (PBMC). After washing in physiological saline, they were suspended in 10% FCS-RPMI. PBMC adjusted to a cell concentration of 2–4×10$^6$/ml was aliquoted in a 48-well culture plate, and cultured together with various concentrations of CpG DNA in a 5% $CO_2$ incubator for 18 to 24 hours. After culturing was complete, the supernatant was collected by centrifugation (5,000 rpm, 3 min). For the culture supernatant, the concentrations of IFN-α, IFN-γ, IL-12, TNF-α, IL-10 and IL-4 were determined using the ELISA Kit (BioSources). CpG DNA was synthesized using the phosphoramidite method, and then excised from the solid-phase carrier, deprotected, and finally purified by gel filtration (referred to Hokkaido System Science). The labware and reagents used were endotoxin-free.

Example 1

Study of the position and the number of Gs added (G0-GACGA-Gn): With GACGATCGTC as the core sequence, 1 to 10 (n) Gs only were added to the 3'-end to synthesize the sequences in the table (Table 1) below, and they were added to PBMC to 5 μM and cultured.

TABLE 1

| Base sequence | Abbreviated sequence |
| --- | --- |
| GACGATCGTCG (SEQ ID NO: 21) | G0-GACGA-G1 |
| GACGATCGTCGG (SEQ ID NO: 22) | G0-GACGA-G2 |
| GACGATCGTCGGG (SEQ ID NO: 23) | G0-GACGA-G3 |
| GACGATCGTCGGGG (SEQ ID NO: 24) | G0-GACGA-G4 |
| GACGATCGTCGGGGG (SEQ ID NO: 25) | G0-GACGA-G5 |
| GACGATCGTCGGGGGG (SEQ ID NO: 26) | G0-GACGA-G6 |
| GACGATCGTCGGGGGGG (SEQ ID NO: 27) | G0-GACGA-G7 |
| GACGATCGTCGGGGGGGG (SEQ ID NO: 28) | G0-GACGA-G8 |
| GACGATCGTCGGGGGGGGG (SEQ ID NO: 29) | G0-GACGA-G9 |
| GACGATCGTCGGGGGGGGGG (SEQ ID NO: 30) | G0-GACGA-G10 |

For the culture supernatant obtained, IFN-α was determined to obtain the result shown in FIG. 1. Up to three-chain G-added GACGATCGTC exhibited no activity of inducing IFN-α production, and activity was induced by the addition of 4 chains or more Gs.

Example 2

Study on the position and the number of Gs added (Gm-GACGA-G0): 5-10(m) Gs only were added to the 5'-end to synthesize the sequences in the table (Table 2) below, and they were added to PBMC to 5 μM and cultured.

TABLE 2

| Base sequence | Abbreviated sequence |
| --- | --- |
| GGGGGGACGATCGTC (SEQ ID NO: 31) | G5-GACGA-G0 |
| GGGGGGGACGATCGTC (SEQ ID NO: 32) | G6-GACGA-G0 |

TABLE 2-continued

| Base sequence | Abbreviated sequence |
| --- | --- |
| GGGGGGGGACGATCGTC (SEQ ID NO: 33) | G7-GACGA-G0 |
| GGGGGGGGGACGATCGTC (SEQ ID NO: 34) | G8-GACGA-G0 |
| GGGGGGGGGGACGATCGTC (SEQ ID NO: 35) | G9-GACGA-G0 |
| GGGGGGGGGGGACGATCGTC (SEQ ID NO: 36) | G10-GACGA-G0 |

Figure 2:
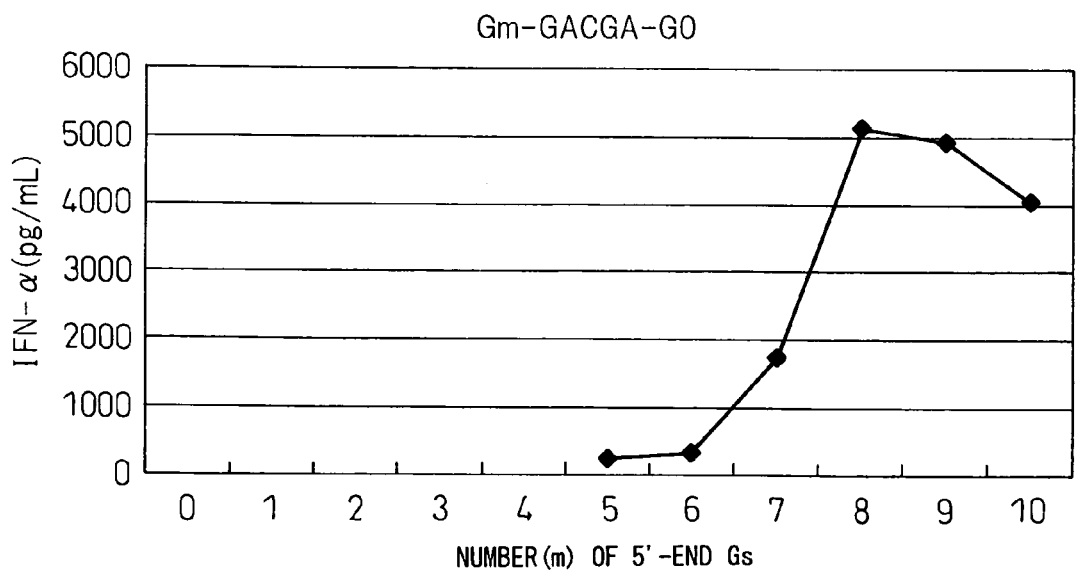
FIG. 2 is a graph showing the result of investigation of the number of Gs added (Gm-GACGA-GO) to the 5'-end in Example 2.

For the culture supernatant obtained, IFN-α was determined to obtain the result shown in FIG. 2. With the addition of 5 to 6 Gs, the activity of inducing IFN-α production was low, and at least 7 Gs were required. With the addition of 8 or 9 Gs, IFN-α production reached a peak.

Example 3

Study on the position and the number of Gs added (Gm-GACGA-G10): By comparing Examples 1 and 2, it was conjectured that G addition to the 3'-end compared to that to the 5'-end can induce activity with a smaller number of Gs and thus has a higher IFN-α-inducing activity. Then, sequences in which the number, m, of Gs is 0 to 5 and 10 with the number of Gs at the 3'-end fixed at 10 were synthesized (Table 3), which were added to PBMC to 5 μM and cultured.

TABLE 3

| Base sequence | Abbreviated sequence |
| --- | --- |
| GACGATCGTCGGGGGGGGGG (SEQ ID NO: 37) | G0-GACGA-G10 |
| GGACGATCGTCGGGGGGGGGG (SEQ ID NO: 38) | G1-GACGA-G10 |
| GGGACGATCGTCGGGGGGGGGG (SEQ ID NO: 39) | G2-GACGA-G10 |
| GGGGACGATCGTCGGGGGGGGGG (SEQ ID NO: 40) | G3-GACGA-G10 |
| GGGGGACGATCGTCGGGGGGGGGG (SEQ ID NO: 41) | G4-GACGA-G10 |
| GGGGGGACGATCGTCGGGGGGGGGG (SEQ ID NO: 42) | G5-GACGA-G10 |
| GGGGGGGGGGACGATCGTCGGGGGGGGGG (SEQ ID NO: 43) | G10-GACGA-G10 |

Figure 3:
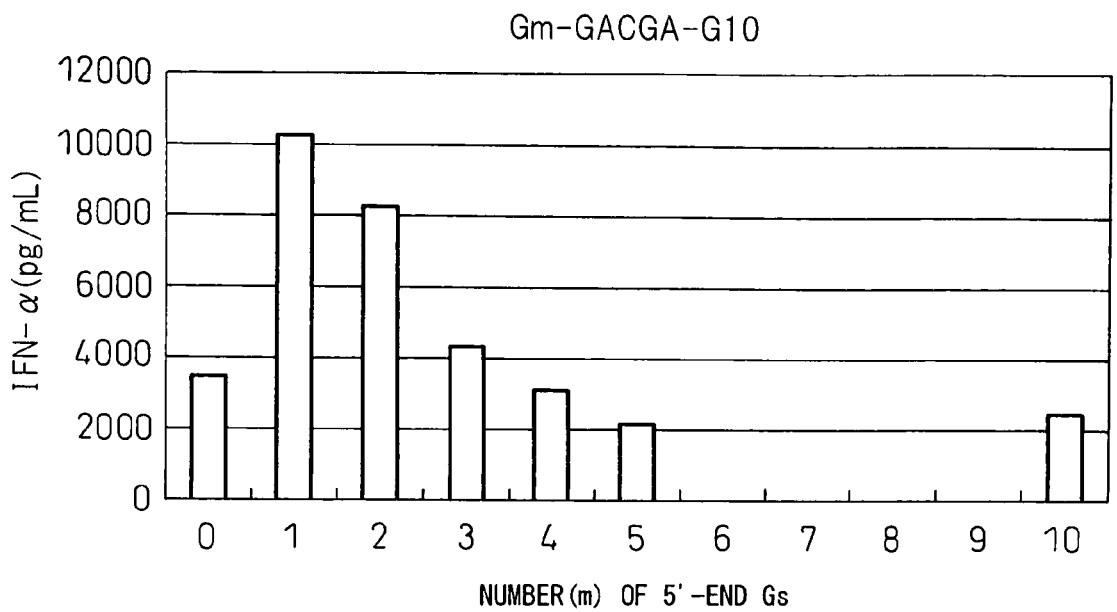
FIG. 3 is a graph showing the result of investigation of the number of Gs added (Gm-GACGA-G10) to the 5'-end while fixing the number of Gs added to the 3'-end at 10 in Example 3.

For the culture supernatant obtained, IFN-α was determined to obtain the result shown in FIG. 3. When 10 chains of G were placed at the 3'-end, the addition of only 1 to 2 chains to the 5'-end enhanced the IFN-α-inducing activity. However, the effect was not proportional to the number of Gs, and with the addition of 3-chain or more Gs the IFN-α-inducing activity tended to decrease.

Example 4

Figure 4:
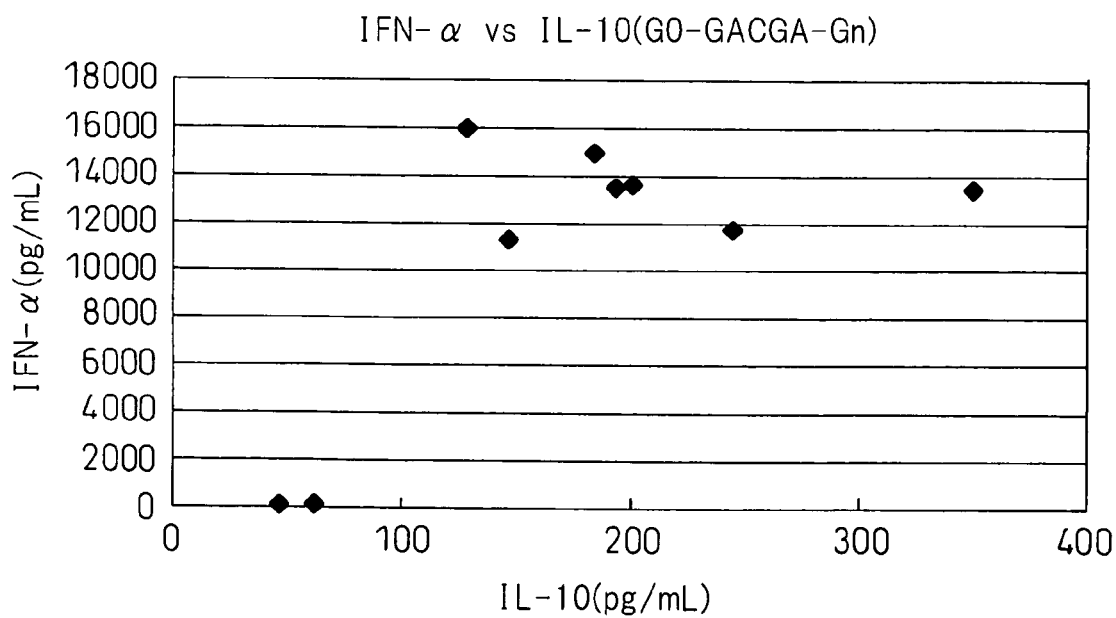
FIG. 4 is a graph showing the result of investigation of the correlation of IFN-α and IL-10 production of GO-GACGA-Gn in Example 4.
Figure 5:
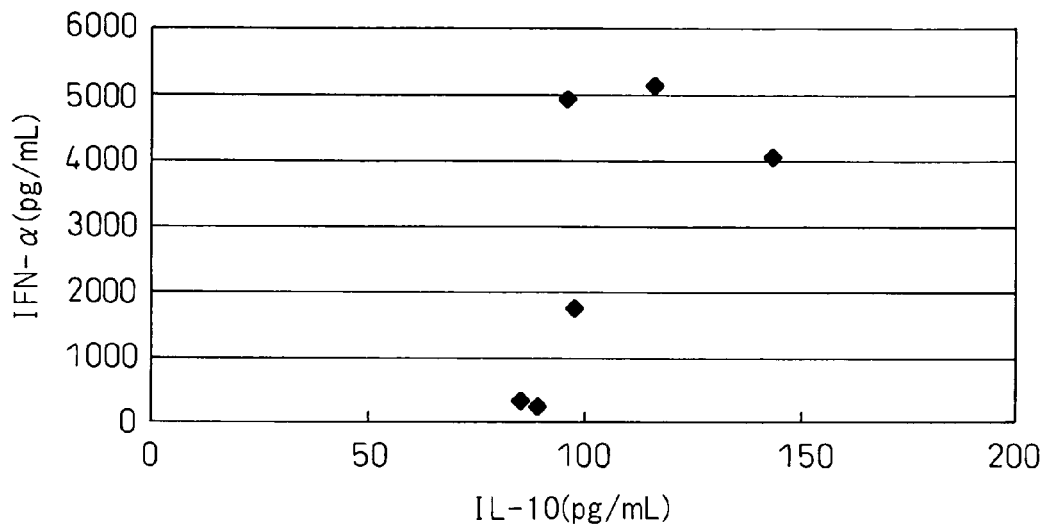
FIG. 5 is a graph showing the result of investigation of the correlation of IFN-α and IL-10 production of Gm-GACGA-GO in Example 4.
Figure 6:
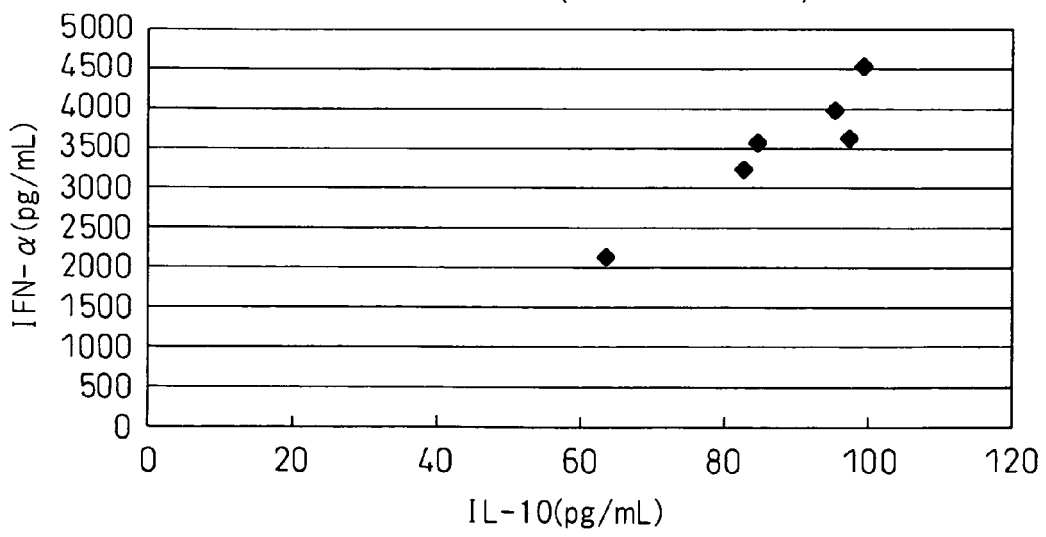
FIG. 6 is a graph showing the result of investigation of the correlation of IFN-α and IL-10 production of Gm-GACGA-G10 in Example 4.

Correlation of IFN-α and IL-10 production: For the sequences studied in Examples 1 to 3, the amounts produced of IFN-α and IL-10 were determined to investigate their relationship (FIGS. 4 to 6). Since IL-10 has an immunosuppressing activity, the purpose was to find sequences that enhance IFN-α production while keeping the IL-10 production as low as possible. The addition of G to the 5'-end with 10-chain Gs being placed on the 3'-end, the IL-10-inducing activity increased in proportion to the enhanced IFN-α-inducing activity, indicating a correlation between the two (FIG. 6), and thus it is not preferred as the sequence of interest. However, there was no definite correlation for the G0-GACGA-Gn type (FIG. 4) or the Gm-GACGA-G0 type (FIG. 5), and specifically for the Gm-GACGA-G0 type, the enhanced IFN-α-inducing activity by G addition was noted while keeping IL-10 production close to the basal level. Therefore it was estimated that, by studying this sequence pattern, preferred sequences that only induce IFN-α may be identified (FIG. 5).

Example 5

Determination of the number of bases: From the results of studies in Examples 1 to 3, it was estimated that 8 to 10 Gs should be placed at the 3'-end or the 5'-end in order to obtain a high IFN-α-inducing activity for GACGATCGTC, while Gs should be unevenly placed at the 5'-end in order to suppress IL-10 production. The optimum total number of bases of CpG DNA required for activity induction was about 20 (Table 4 below).

TABLE 4

CpG DNA having a high ability of producing IFN-α

| Base sequence | Optimum number of Gs (m, n) | Total number of bases of CpG-DNA |
|---|---|---|
| G0-GACGATCGTC-Gn | n = 8-10 | 18-20 |
| Gm-GACGATCGTC-G0 | m = 8-10 | 18-20 |
| Gm-GACGATCGTC-G10 | m = 1-2 | 21-22 |

Based on the above conclusion, the IFN-α-inducing activity of poly G-added palindrome CpG DNA was investigated with the total number of bases fixed at 20.

Example 6

Induction of IFN-α in Gm-GACGATCGTC-Gn: Eleven oligonucleotides of Gm-GACGATCGTC-Gn (Table 5 below) were synthesized in which the total number of the number, m, of Gs at the 5'-end, and the number, n, of Gs at the 3'-end combined, was fixed at 10 (m+n=10), and were added to PBMC to 5 μM, and cultured.

TABLE 5

| Base sequence | Number of Gs (m + n = 10) |
|---|---|
| GACGATCGTCGGGGGGGGGG (SEQ ID NO: 44) | m = 0, n = 10 |
| GGACGATCGTCGGGGGGGGG (SEQ ID NO: 13) | m = 1, n = 9 |
| GGGACGATCGTCGGGGGGGG (SEQ ID NO: 14) | m = 2, n = 8 |
| GGGGACGATCGTCGGGGGGG (SEQ ID NO: 15) | m = 3, n = 7 |

TABLE 5-continued

| Base sequence | Number of Gs (m + n = 10) |
|---|---|
| GGGGGACGATCGTCGGGGGG (SEQ ID NO: 45) | m = 4, n = 6 |
| GGGGGGACGATCGTCGGGGG (SEQ ID NO: 46) | m = 5, n = 5 |
| GGGGGGGACGATCGTCGGGG (SEQ ID NO: 16) | m = 6, n = 4 |
| GGGGGGGGACGATCGTCGGG (SEQ ID NO: 17) | m = 7, n = 3 |
| GGGGGGGGGACGATCGTCGG (SEQ ID NO: 18) | m = 8, n = 2 |
| GGGGGGGGGGACGATCGTCG (SEQ ID NO: 19) | m = 9, n = 1 |
| GGGGGGGGGGGACGATCGTC (SEQ ID NO: 47) | m = 10, n = 0 |

Figure 7:
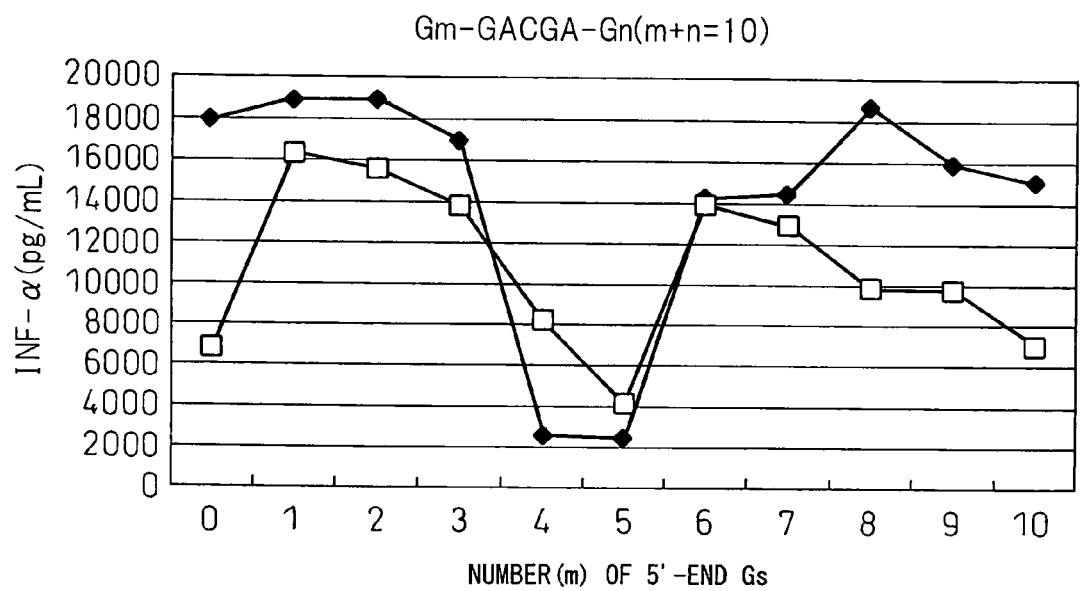
FIG. 7 is a graph showing the result of investigation of the effect of the position and the number of Gs added (Gm-GACGA-Gn) on IFN-α induction in Example 6.

As a result, the production of a large quantity of IFN-a was induced with m=1 to 3 (n=9 to 7) and m=6 to 9 (n=4 to 1). However, at m=4 (n=6) and m=5 (n=5) the production of IFN-α markedly decreased (FIG. 7).

Example 7

Figure 8:
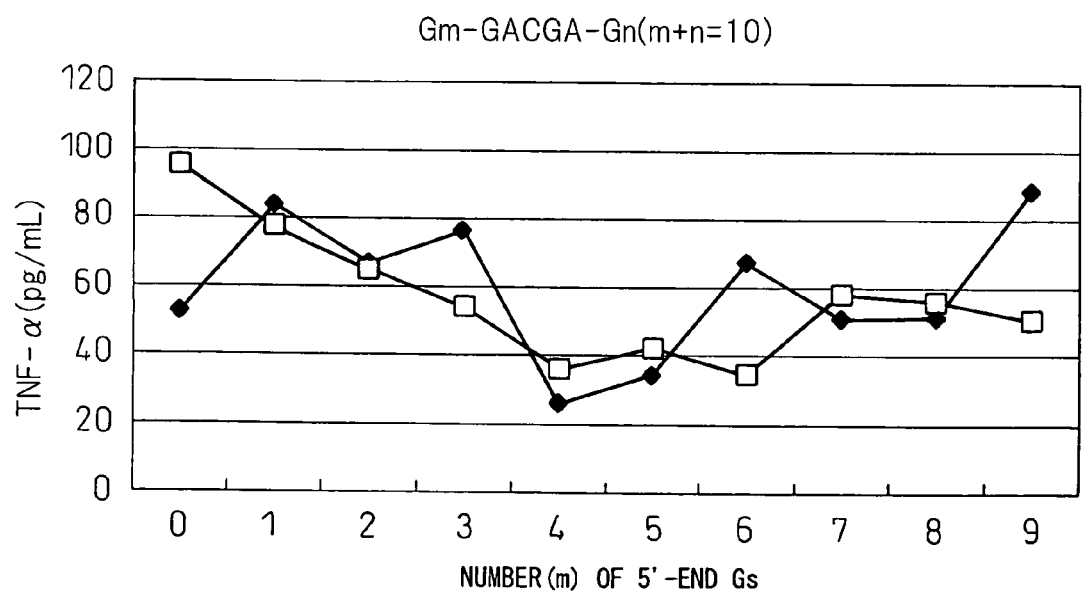
FIG. 8 is a graph showing the result of investigation of the effect of the position and the number of Gs added (Gm-GACGA-Gn) on TNF-α induction in Example 7.

Induction of TNF-α in Gm-GACGATCGTC-Gn: Ten oligonucleotides (m=0 to 9) represented by Gm-GACGA-Gn (m+n=10) represented by similar sequences to those in Example 6 were added to PBMC to 5 μM and cultured, and the amount produced of TNF-α in the supernatant was determined (FIG. 8). The production of TNF-α for each sequence exhibits the same pattern as the production of IFN-α, and a slight correlation was noted between the activities of the two.

Example 8

Figure 9:
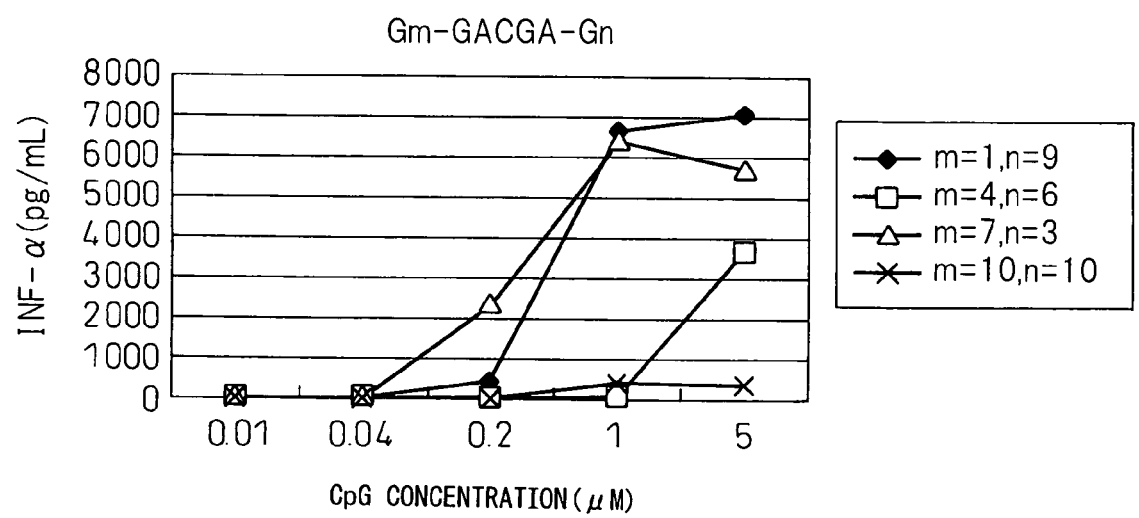
FIG. 9 is a graph showing the result of investigation (1) (Gm-GACGA-Gn) of activity strength in terms of doses and activity in Example 8.

Investigation of activity strength in terms of doses and activity (1): In order to investigate the activity strength of ten oligonucleotides represented by Gm-GACGA-Gn (m+n=10), comparison was made at 5 levels of concentrations from 0.01 to 5 μM added to PBMC (FIG. 9). As a result, at m=7 (n=3) and m=1 (n=9), very strong IFN-α production was noted. In contrast, at m=4 (n=6) and m=10, n=10, the activity was low.

Example 9

Figure 10:
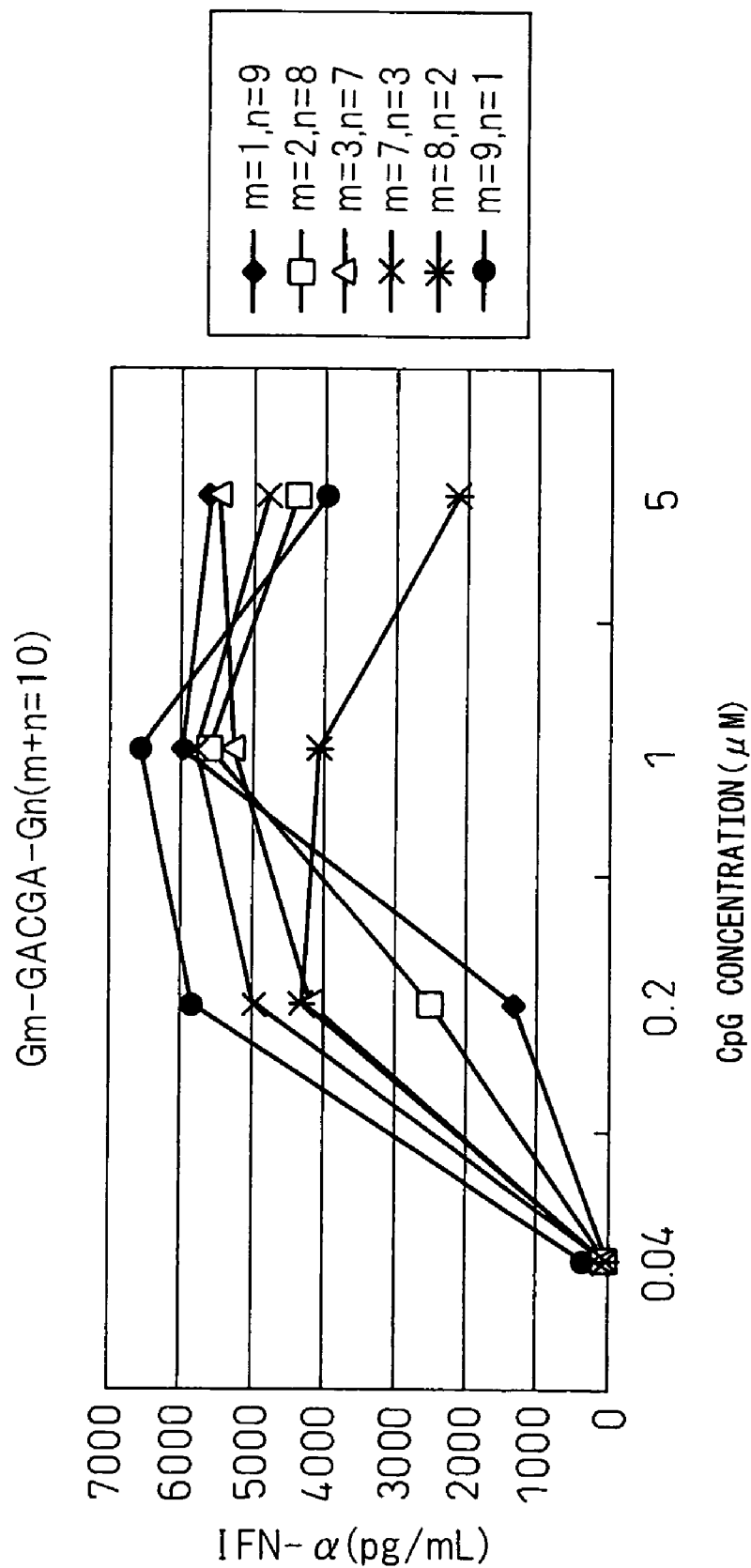
FIG. 10 is a graph showing the result of investigation (2) (Gm-GACGA-Gn) of activity strength in terms of doses and activity in Example 9.

Investigation of activity strength in terms of doses and activity (2): In order to investigate in detail the activity strength of oligonucleotides represented by Gm-GACGA-Gn (m+n=10) investigated in Example 8, m=7, 8 and 9 (n is 3, 2 and 1, respectively) were investigated (FIG. 10). As a result, for the oligonucleotide with m=9 (n=1), the maximum IFN-α-inducing activity was noted.

Example 10

Figure 11:
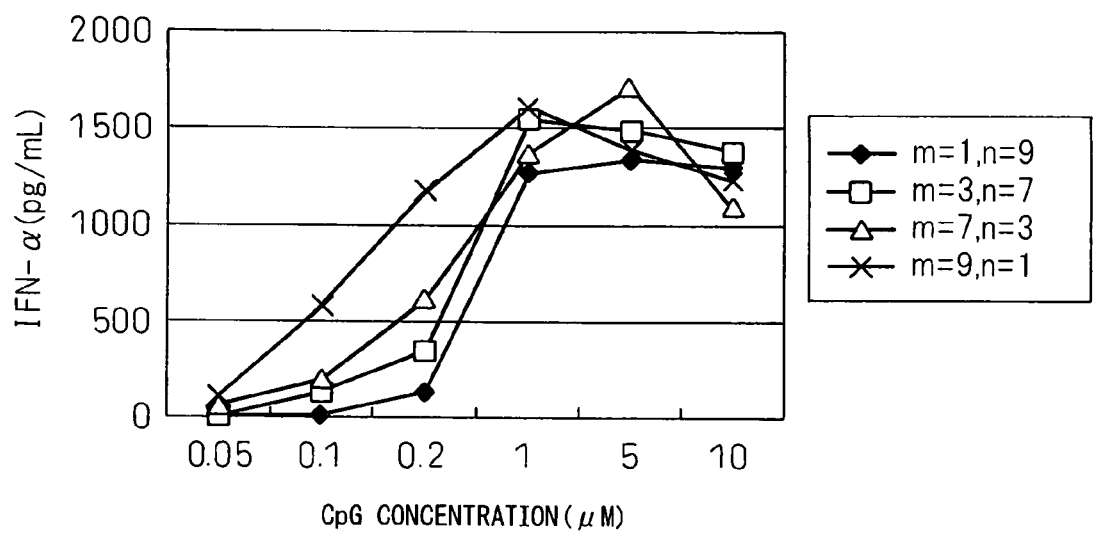
FIG. 11 is a graph showing the result of investigation of a wide range of doses in Example 10.

Investigation for a wide range of doses: It was investigated in detail how the IFN-α-inducing activity of oligonucleotides represented by Gm-GACGA-Gn (m+n=10) changes in the low concentration range and the high concentration range of CpG DNA. Six levels of concentrations from 0.05 to 10 μM added to PBMC were investigated (FIG. 11). As a result, CpG DNA with m=9 (n=1) exhibited an inducing activity even at a concentration of 0.1 μM, the concentration at which other oligonucleotides hardly induced the production of IFN-α. The maximum activity was shown at a concentration of 1 μM and activity was retained up to 10 μM.

Example 11

Figure 12:
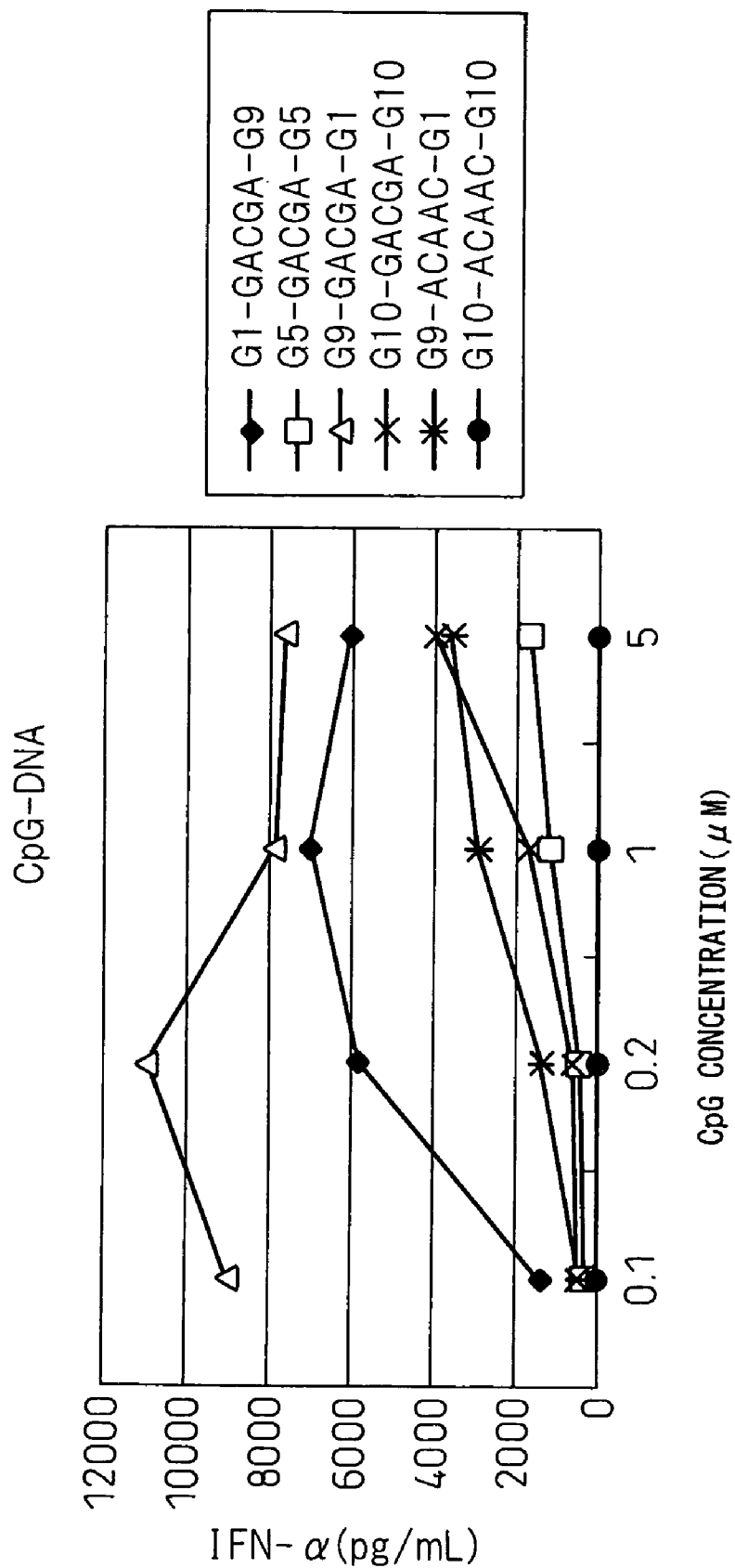
FIG. 12 is a graph showing the result of investigation (1) of the significance of the palindrome sequence of G9-GACGA-G1 in Example 11.

Significance of the palindrome core base sequence: As described above, in the investigation on poly G on both ends of the core sequence GACGATCGTC (SEQ. ID. NO. 12), a potent IFN-α-inducing activity was obtained in G9-GACGA-G1 in which 9 chains were added to the 5'-end and one chain G was added to the 3'-end. Regarding whether or not a similar effect of the position of G could be recognized for CpG palindromes in which the core sequence is different, the following (Table 6) ACAACGTTGT (SEQ. ID. NO. 48) was investigated (FIG. 12, 13). G addition was effected in four cases of m=9 (n=1), m=5 (n=5), m=1 (n=9), and m=10 (n=10).

TABLE 6

| Base sequence | Abbreviated sequence |
| --- | --- |
| GGACGATCGTCGGGGGGGGG (SEQ ID NO: 13) | G1-GACGA-G9 |
| GACAACGTTGTGGGGGGGGG (SEQ ID NO: 49) | G1-ACAAC-G9 |
| GGGGGGACGATCGTCGGGGG (SEQ ID NO: 46) | G5-GACGA-G5 |
| GGGGGACAACGTTGTGGGGG (SEQ ID NO: 50) | G5-ACAAC-G5 |
| GGGGGGGGGGACGATCGTCG (SEQ ID NO: 19) | G9-GACGA-G1 |
| GGGGGGGGGACAACGTTGTG (SEQ ID NO: 51) | G9-ACAAC-G1 |
| GGGGGGGGGGACGATCGTCGGGGGGGGGG (SEQ ID NO: 47) | G10-GACGA-G10 |
| GGGGGGGGGGACAACGTTGTGGGGGGGGGG (SEQ ID NO: 52) | G10-ACAAC-G10 |

When Gs were added to GACGATCGTC, as described above, activity was high in the following order: m=9 (n=1) >m=1 (n=9)>m=10 (n=10)>m=5 (n=5) (FIG. 12). When Gs were added to ACAACGTTGT, the activity was markedly low as compared to GACGATCGTC though the relation of the position of addition and activity enhancement was the same (FIG. 13). Thus, though the addition of poly G is very important for enhancement of activity of the palindrome CpG DNA, the site that most contributed to the expression of activity is the core sequence of the palindrome CpG DNA.

Specifically explained, as shown in FIGS. 12 and 13, a potent IFN-α-inducing activity was noted for G9-GACGA-G1 (SEQ. ID. NO. 19) and G1-GACGA-G9 (SEQ. ID. NO. 13), and the results shown in the above Examples 8 to 10 were reproduced. For ACAAC having a different core sequence, little IFN-α-inducing activity was noted in G10-ACAAC-G10 (SEQ. ID. NO. 52) in which a poly G sequence was introduced (FIG. 12, FIG. 13), whereas in G9-ACAAC-G1 (SEQ. ID. NO. 51) a IFN-α-inducing activity similar to the G10-GACGA-G10 (SEQ. ID. NO. 47) conventionally used by the present inventors was noted (FIG. 12). Furthermore, when GACGATCGTC (SEQ. ID. NO. 12) was used in the core sequence, there was a marked difference in the IFN-α-inducing activity between G9-GACGA-G1 (SEQ. ID. NO. 19) and G1-GACGA-G9 (SEQ. ID. NO. 13), (FIGS. 12 and 13), but when ACAACGTTGT (SEQ. ID. NO. 48) was used in the core sequence, no major differences were was noted between G9-ACAAC-G1 (SEQ. ID. NO. 51) and G1-ACAAC-G9 (SEQ. ID. NO. 49) (FIG. 13).

From the foregoing, the addition of Gs under the optimum condition is believed to be useful for enhancing the immunostimulatory activity of CpG DNA. However, the site where CpG DNA most contributes to the original immunostimulatory activity is the base sequence of the palindrome portion of the center of CpG DNA. The most important part of the present invention is the use of 5'-GACGATCGTC-3' as the core sequence and the introduction of unmodified (diester type) Gs of an optimum length on both ends of the core sequence. Ultimately the sequence of the entire 20 bases of CpG DNA is important for the immunostimulatory activity. Among the base sequences the inventors have studied on the induction of IFN-α as the immunostimulatory activity, the base sequence of G9-GACGATCGTC-G1 had the most potent activity.

Example 12

Study of the mutants of GACGATCGTC (SEQ. ID. NO. 12): Finally, as shown below (Table 7), the inventors studied how the modification of the base sequence of the palindrome portion of G9-GACGA-G1 (GACGATCGTC) affects the IFN-α-inducing activity (FIG. 14). Activity disappeared when CG was replaced with GC (GAGCATGCTC (SEQ. ID. NO. 53)) while maintaining the palindrome structure. Also, when AT was replaced with AA (GACGAACGTC (SEQ. ID. NO. 54)) or AT with TT (GACGTTCGTC (SEQ. ID. NO. 55)) and the head of the center portion is made a non-palindrome structure, the IFN-α-inducing activity disappeared. Furthermore, it was confirmed that the mere conversion of AT to TA (GACGTACGTC (SEQ. ID. NO. 56)) while maintaining the CpG palindrome structure leads to almost complete loss of the immunostimulatory activity. A sequence (CACGATCGTG (SEQ. ID. NO. 52)) in which G was replaced with C at the 5'-end of the CpG palindrome and C was replaced with G at the 3'-end exhibits an activity similar to G9-GACGATCGTC-G1 (SEQ. ID. NO. 19) at high concentrations, but the produced amount of IFN-α decreased by 30-40% at concentrations of 0.1 to 0.2 μM.

TABLE 7

| Type of CpG DNA | Abbreviated sequence | Amount produced of IFN-α when 1 μM of CpG DNA was acted (pg/ml) |
| --- | --- | --- |
| GGGGGGGGGGACGATCGTCG (SEQ ID NO: 19) | (G9-GACGA-G1) | 8,060 |
| GGGGGGGGGGA<u>G</u>CATG<u>C</u>TCG (SEQ ID NO: 58) | (G9-GAGCA-G1) | 119 |
| GGGGGGGGGGACG<u>TA</u>CGTCG (SEQ ID NO: 59) | (G9-GACGT-G1) | 135 |
| GGGGGGGGGGACGA<u>A</u>CGTCG (SEQ ID NO: 60) | (G9-GACGAA-G1) | 56 |
| GGGGGGGGGGACG<u>TT</u>CGTCG (SEQ ID NO: 61) | (G9-GACGTT-G1) | 49 |

TABLE 7-continued

| Type of CpG DNA | Abbreviated sequence | Amount produced of IFN-α when 1 μM of CpG DNA was acted (pg/ml) |
|---|---|---|
| GGGGGGGGGCACGATCGTGG (SEQ ID NO: 62) | (G9-CACGA-G1) | 7,050 |

Example 13

Production of the Th1 type cytokine and the Th2 type cytokine of G9-GACGA-G1 (SEQ. ID. NO. 19): In order to investigate whether or not the activity of G9-GACGA-G1 (SEQ. ID. NO. 19) acts dominantly in the induction of Th1 immunity, the production of IL-12 and IFN-γ, in addition to IFN-α, as an index of the Th1 type immunity and IL-4 as an index of the Th2 type immunity was determined. For each CpG DNA shown in the table (Table 8) below, the amount produced of cytokine in the culture supernatant obtained when added to PBMC to 1 μM was investigated.

TABLE 8

| Base sequence | Th1 type cytokine | | Th2 type cytokine |
|---|---|---|---|
| | IL-12 | IFN-γ | IL-4 |
| Experiment 1 (pg/mL) | | | |
| G1-GACGA-G9 (SEQ ID NO: 13) | 33.9 | 17.4 | Below the detection limit |
| G5-GACGA-G5 (SEQ ID NO: 46) | 26.7 | 9.5 | Below the detection limit |
| G9-GACGA-G1 (SEQ ID NO: 19) | 44.2 | 12.9 | Below the detection limit |
| G10-GACGA-G10 (SEQ ID NO: 47) | 20.7 | 16.9 | Below the detection limit |
| Experiment 2 (pg/mL) | | | |
| G1-GACGA-G9 (SEQ ID NO: 13) | 16.5 | 14.1 | Below the detection limit |
| G9-GACGA-G1 (SEQ ID NO: 19) | 23.1 | 14.5 | Below the detection limit |

As described above (Table 8), from the result of the second experiment, IL-12 secreted as a Th1 type cytokine from myeloid dendritic cells or macrophage-like cells was induced from any sequence, but was induced in G9-GACGA-G1 (SEQ. ID. NO. 19) more strongly than in G1-GACGA-G9 (SEQ. ID. NO. 13). Though the production of IFN-γ was also noted, there was no difference between G1-GACGA-G9 (SEQ. ID. NO. 13) and G9-GACGA-G1 (SEQ. ID. NO. 19). The amount of IL-4 that was determined as a Th2 type cytokine was below the detection limit in any sample. From the results, G9-GACGA-G1 and G1-GACGA-G9 are suggested to make a Th1-dominant immune state in humans, by inducing the production of Th1 type cytokines, such as IFN-γ and IL-12, without inducing the production of the Th2 type cytokine IL-4.

INDUSTRIAL APPLICABILITY

The oligonucleotide of the present invention can potently induce the production of IFN-α by acting on peripheral blood mononuclear cells to stimulate and activation the immune system of the subject administered. It can also enhance the Th1 immune response such as IL-12 and IFN-γ. Thus, the present invention is useful as a vaccine adjuvant for tuberculosis or hepatitis, and can be used for the prevention and treatment of infections by viruses, bacteria, fungi etc., and allergy diseases, and prevention and treatment of cancer.

The invention claimed is:

1. An immunostimulatory oligonucleotide that consists of the following base sequence:
GGGGGGGGGGACGATCGTCG (SEQ ID NO: 19).

2. A pharmaceutical formulation comprising as an active ingredient an immunostimulatory oligonucleotide consisting of the base sequence GGGGGGGGGGACGATCGTCG (SEQ ID NO: 19).

3. A pharmaceutical formulation comprising as an active ingredient an immunostimulatory oligonucleotide consisting of the base sequence GGGGGGGGGGACGATCGTCG (SEQ ID NO: 19), and further comprising an immunomodulating factor.

4. A pharmaceutical formulation according to claim 3 wherein said immunomodulating factor is an antigen or an adjuvant.

* * * * *